| (12) | United States Patent<br>Tegg | (10) Patent No.: US 9,532,830 B2<br>(45) Date of Patent: Jan. 3, 2017 |

(54) CATHETER WITH A MECHANISM FOR OMNI-DIRECTIONAL DEFLECTION OF CATHETER SHAFT

(71) Applicant: ST. JUDE MEDICAL, CARDIOLOGY DIVISION, INC., St. Paul, MN (US)

(72) Inventor: Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 14/208,648

(22) Filed: Mar. 13, 2014

(65) Prior Publication Data

US 2014/0194718 A1      Jul. 10, 2014

Related U.S. Application Data

(63) Continuation of application No. 12/847,225, filed on Jul. 30, 2010, now Pat. No. 8,696,620.

(51) Int. Cl.
 *A61B 18/14*      (2006.01)
 *A61M 25/01*     (2006.01)
 (Continued)

(52) U.S. Cl.
 CPC ........... *A61B 18/1492* (2013.01); *A61B 5/042* (2013.01); *A61B 5/6852* (2013.01);
 (Continued)

(58) Field of Classification Search
 CPC ....................... A61M 25/0041; A61M 25/0662
 (Continued)

(56) References Cited

U.S. PATENT DOCUMENTS

| 4,013,080 A | 3/1977 | Froning |
| 4,518,383 A | 5/1985 | Evans |

(Continued)

FOREIGN PATENT DOCUMENTS

WO     WO 97/21462      6/1997

OTHER PUBLICATIONS

International Search Report and Written Opinion for PCT/US2008/085184 mailed Feb. 17, 2009.

(Continued)

*Primary Examiner* — Scott Medway
(74) *Attorney, Agent, or Firm* — Dykema Gossett PLLC

(57) ABSTRACT

A catheter with a mechanism for omni-directional deflection of a catheter shaft includes a shaft assembly and a controller. The shaft assembly includes a first tubular component that has a preformed curvilinear distal section, a second, substantially straight tubular component with a main axis and an outer shaft. The first and second components are configured for slidable movement therebetween while preserving common rotation so that when the second component is axially moved in a distal direction, the second component deflects the preformed curvilinear section towards the main axis while orientation of the outer shaft is preserved. The controller is configured to effect relative axial movement between the first and second components as well as to effect rotation of the first and second components (and thus also of the preformed curvilinear distal section) without any rotation of the shaft relative to the handle. Varying the deflection of the preformed curvilinear section in combination with variable rotational movement achieves omni-directional distal tip bending.

23 Claims, 27 Drawing Sheets

(51) Int. Cl.
*A61B 5/042* (2006.01)
*A61B 5/00* (2006.01)
A61M 25/00 (2006.01)
A61N 1/05 (2006.01)

(52) U.S. Cl.
CPC ....... *A61M 25/0136* (2013.01); *A61M 25/007* (2013.01); *A61N 1/056* (2013.01); *Y10T 29/49826* (2015.01)

(58) Field of Classification Search
USPC .......................................... 604/95.01–95.04
See application file for complete search history.

(56) References Cited

U.S. PATENT DOCUMENTS

| | | | |
|---|---|---|---|
| 4,909,798 A | 3/1990 | Fleischhacker et al. | |
| 5,114,408 A | 5/1992 | Fleischhaker et al. | |
| 5,219,358 A | 6/1993 | Bendel et al. | |
| 5,221,269 A | 6/1993 | Miller et al. | |
| 5,231,989 A | 8/1993 | Middleman et al. | |
| 5,238,004 A | 8/1993 | Sahatjian et al. | |
| 5,242,448 A | 9/1993 | Pettine et al. | |
| 5,265,822 A | 11/1993 | Shober et al. | |
| 5,385,561 A * | 1/1995 | Cerny ........................... | 604/264 |
| 5,397,304 A | 3/1995 | Truckai | |
| 5,427,119 A | 6/1995 | Swartz et al. | |
| 5,497,774 A | 3/1996 | Swartz et al. | |
| 5,501,694 A | 3/1996 | Ressemann | |
| 5,564,440 A | 10/1996 | Swartz et al. | |
| 5,575,766 A | 11/1996 | Swartz et al. | |
| 5,601,572 A | 2/1997 | Middleman et al. | |
| 5,607,389 A | 3/1997 | Edwards et al. | |
| 5,624,396 A | 4/1997 | McNamara et al. | |
| 5,628,316 A | 5/1997 | Swartz et al. | |
| 5,628,734 A | 5/1997 | Hatfalvi | |
| 5,640,955 A | 6/1997 | Ockuly et al. | |
| 5,690,611 A | 11/1997 | Swartz et al. | |
| 5,715,818 A | 2/1998 | Swartz et al. | |
| 5,725,512 A | 3/1998 | Swartz et al. | |
| 5,782,797 A | 7/1998 | Schweich et al. | |
| 5,833,673 A | 11/1998 | Ockuly et al. | |
| 5,868,733 A | 2/1999 | Ockuly | |
| 5,879,296 A | 3/1999 | Ockuly et al. | |
| 5,987,344 A | 11/1999 | West | |
| 6,066,126 A | 5/2000 | Li et al. | |
| 6,090,084 A | 7/2000 | Hassett et al. | |
| 6,156,018 A | 12/2000 | Hassett | |
| 6,176,825 B1 | 1/2001 | Chin et al. | |
| 6,190,353 B1 | 2/2001 | Makower et al. | |
| 6,233,476 B1 | 5/2001 | Strommer et al. | |
| 6,258,084 B1 | 7/2001 | Goldman et al. | |
| 6,478,776 B1 * | 11/2002 | Rosenman et al. ...... | 604/164.01 |
| 6,526,302 B2 | 2/2003 | Hassett | |
| 6,540,755 B2 | 4/2003 | Ockuly et al. | |
| 6,572,593 B1 | 6/2003 | Daum | |
| 6,592,559 B1 | 7/2003 | Pakter et al. | |
| 6,607,496 B1 | 8/2003 | Poor et al. | |
| 6,616,628 B2 | 9/2003 | Hayzelden | |
| 6,690,963 B2 | 2/2004 | Ben-Haim et al. | |
| 7,022,102 B2 | 4/2006 | Paskar | |
| 7,066,942 B2 | 6/2006 | Treace | |
| 7,101,361 B2 | 9/2006 | Gardeski | |
| 7,160,296 B2 | 1/2007 | Pearson et al. | |
| 7,197,354 B2 | 3/2007 | Sobe | |
| 7,263,397 B2 | 8/2007 | Hauck et al. | |
| 7,276,032 B2 | 10/2007 | Hibner | |
| 7,300,438 B2 | 11/2007 | Falwell et al. | |
| 7,386,339 B2 | 6/2008 | Strommer et al. | |
| 7,536,218 B2 | 5/2009 | Govari et al. | |
| 7,713,273 B2 | 5/2010 | Krueger et al. | |
| 7,815,571 B2 | 10/2010 | Deckman et al. | |
| 7,842,041 B2 | 11/2010 | Liu et al. | |
| 8,043,251 B2 | 10/2011 | Nita et al. | |
| 8,048,030 B2 | 11/2011 | McGuckin et al. | |
| 8,083,708 B2 | 12/2011 | Flaherty et al. | |
| 8,172,772 B2 | 5/2012 | Zwolinski et al. | |
| 8,214,015 B2 | 7/2012 | Macaulay et al. | |
| 2002/0032359 A1 | 3/2002 | Geoffrion et al. | |
| 2002/0087076 A1 | 7/2002 | Meguro et al. | |
| 2003/0114844 A1 | 6/2003 | Ormsby | |
| 2003/0212394 A1 | 11/2003 | Pearson et al. | |
| 2005/0070844 A1 | 3/2005 | Chow et al. | |
| 2006/0142694 A1 | 6/2006 | Bednarek et al. | |
| 2006/0151923 A1 | 7/2006 | Wilkowske et al. | |
| 2006/0252993 A1 | 11/2006 | Freed | |
| 2006/0270976 A1 | 11/2006 | Savage et al. | |
| 2006/0271032 A1 | 11/2006 | Chin et al. | |
| 2006/0287581 A1 | 12/2006 | Ito | |
| 2007/0260115 A1 | 11/2007 | Brock et al. | |
| 2008/0086110 A1 | 4/2008 | Galdonik et al. | |
| 2008/0243064 A1 | 10/2008 | Stahler | |
| 2008/0287862 A1 | 11/2008 | Weitzner | |
| 2009/0171272 A1 | 7/2009 | Tegg et al. | |
| 2009/0171348 A1 | 7/2009 | Guo et al. | |
| 2009/0259126 A1 * | 10/2009 | Saal et al. ..................... | 600/433 |
| 2009/0287210 A1 | 11/2009 | Kauphusman et al. | |
| 2010/0036245 A1 | 2/2010 | Yu et al. | |

OTHER PUBLICATIONS

International Search Report for PCT Application No. PCT/US2011/041405 dated Oct. 18, 2011, 3 pgs.

* cited by examiner

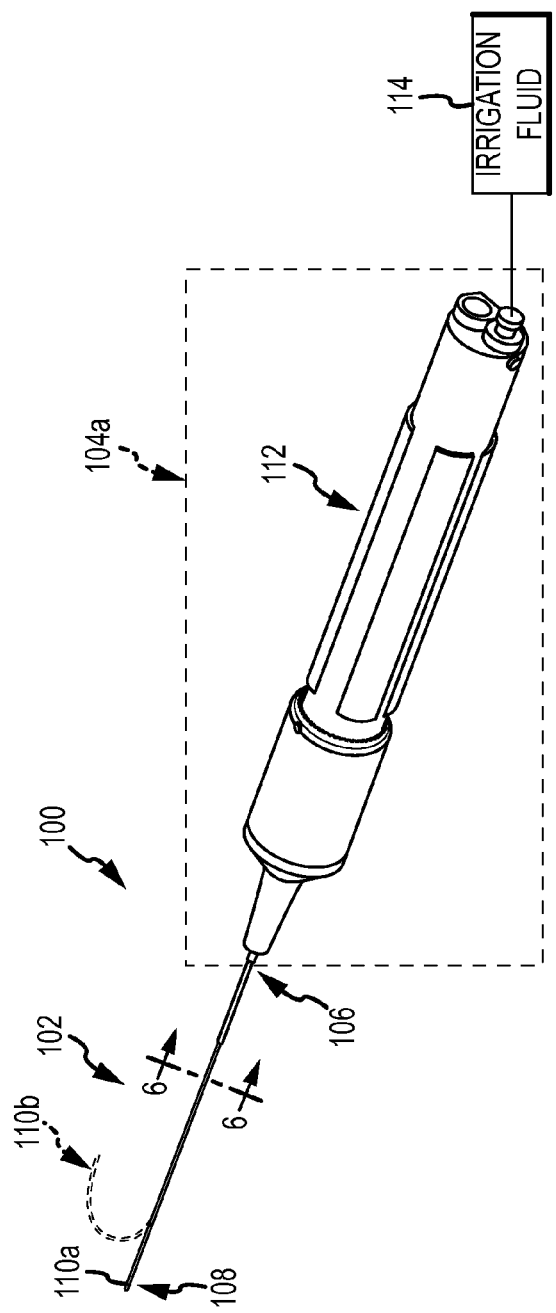
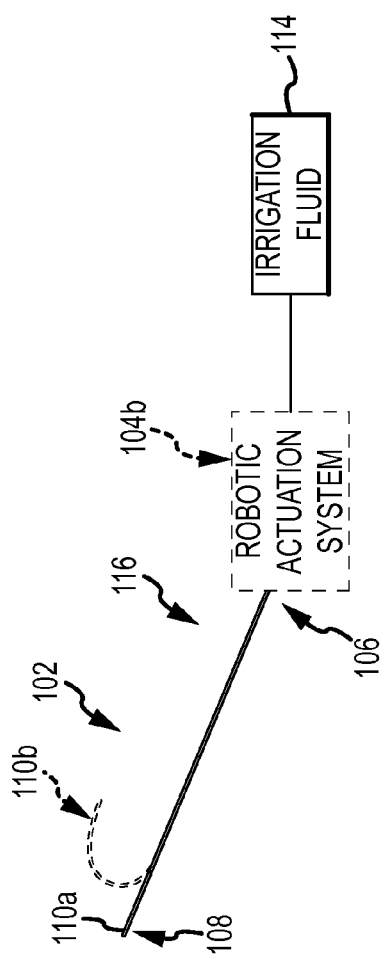
FIG. 1
FIG. 2

CATHETER WITH A MECHANISM FOR OMNI-DIRECTIONAL DEFLECTION OF CATHETER SHAFT

CROSS-REFERENCE TO RELATED APPLICATIONS

This application is a continuation of U.S. application Ser. No. 12/847,225 filed 30 Jul. 2010, now pending, which is hereby incorporated by reference as though fully set forth herein.

BACKGROUND OF THE INVENTION a. Field of the Invention

The present invention relates generally to medical devices and more particularly to a family of electrophysiology (EP) catheters with a mechanism for omni-directional deflection of a catheter shaft which mechanism is free of so-called pull wires or other mechanical tensioning components.

b. Background Art

Many medical procedures require the introduction of specialized medical devices in and around the human heart. Such specialized devices include introducers, access sheaths, catheters, dilators, needles, and the like. Such devices may be used to access areas of the heart, such as the atria or ventricles, and have been used in such medical procedures for a number of years. During such a procedure, a physician typically maneuvers the device through the vasculature of a patient. Accordingly, such devices preferably exhibit at least some degree of flexibility to allow for such maneuvering. To achieve flexibility, pull wires may be provided, which are used to control the movement and relative curvature of the devices. Pull wires extend generally along the length of the device (i.e., typically within an outer wall), and may be coupled at the distal end to a pull ring and at the proximal end to a control mechanism. A typical control mechanism may be, for example, a user-actuated knob that can be rotated, which in turn "pulls" one or more of the pull wires in a predetermined fashion, resulting in the desired deflection.

Repeated deflections of the catheter distal end through use of the pull wires, however, may cause a compression of the catheter shaft at the distal end. Compression causes the catheter shaft to lose its original shape, dimension (e.g., axial dimension), and deflectability. In addition, entanglements of the pull wires during catheter deflection are also known to occur, which may limit the functionality and operability of the device. Moreover, bi-directional deflection of a catheter distal end portion has conventionally been implemented using a pair of diametrically opposing pull wires in combination with manual rotation of the entire catheter shaft about a main axis. Also, applicant is aware of catheter shafts housing four discrete pull wires each oriented at 90 degrees from adjacent wires. However, in some circumstances, it may be undesirable to allow rotation of the outer catheter shaft, for example, when a directional energy delivery/sensing component or an imaging sensor or the like is coupled to a portion of the distal end and thus maintaining or having consistent orientation of such components or sensors is paramount for precise operation.

There is therefore a need for a catheter that minimizes or eliminates one or more of the problems set forth above.

BRIEF SUMMARY OF THE INVENTION

One advantage of the methods and apparatuses described, depicted and claimed herein relates to a catheter with omni-directional deflection capability that is achieved without the use of pull wires or the like. Another advantage relates to a catheter that does not suffer from the adverse effects of shaft compression and potential temporary or permanent deformation that can occur from repeated distal tip deflection during a prolonged EP procedure. A still further advantage relates to a catheter with omni-directional deflection capability that is achieved without rotation of the outer shaft thereby retaining the orientation of each 'face' of the distal end portion of an EP catheter during clinical procedures.

A catheter configured for omni-directional distal bending includes a first tubular component, a second tubular component, a shaft and a controller. The first tubular component has distal and proximal portions where the proximal portion is substantially linear and the distal portion includes a preformed curvilinear section. The curvilinear section may be any arbitrary shape (e.g., any regular shape such as a C-shape, an S-shape, a circular shape, and a multi-revolution shape or any irregular shape, etc.). The second tubular component has distal and proximal portions and is substantially straight and may be fabricated of a material that is more rigid than the first component so that the second tubular component can control the first tubular component as described and depicted herein. In an embodiment, the first and second components are disposed in a concentric relationship, wherein the second, substantially straight component is disposed outside the first, inner component. The first and second components are configured for individual slidable movement therebetween and common rotational movement so as to allow a distal end of the second component to bear against the preformed curvilinear section of the first component while at the same time maintaining common rotation between the first and second components. The shaft is disposed outside of the first and second tubular components and includes an inner lumen configured to accommodate the first and second components.

The substantially straight component is more rigid than the preformed curvilinear section. Accordingly, relative sliding movement of the straight component in the direction of the preformed curvilinear section causes the curvilinear section to deflect away from its preformed shape (i.e., toward a main axis). Conversely, sliding movement of the substantially straight component in a direction away from the curvilinear section allows the curvilinear section to return to the preformed shape. In an embodiment, the first component may comprise shape memory alloys (SMA), such as NITINOL or the like.

The controller includes a base (e.g., a housing in a manually-actuated handle embodiment) and is configured (i) to effect a relative axial movement between the first and second components and (ii) to effect a common rotation of the first and the second components while the shaft remains in a fixed rotational position relative to the base. The axial movement adjusts the degree of deflection of the preformed curvilinear section, which in combination with the rotation of the first and second components (to adjust orientation) achieves omni-directional deflection. In alternate embodiments, the controller includes one of a wholly- or partially-robotic actuation system, wherein in the latter case manual control can be a primary or a back-up configuration.

In an embodiment, the controller is included as part of a catheter handle. The controller includes a knob configured for manual actuation thereof, and a first mechanism or means responsive to actuation of the knob configured to axially move the second (substantially "straight") tubular component relative to the first component. As described above, such axial movement adjusts the shape of the preformed curvilinear section. The controller also includes a second mechanism or means responsive to actuation of the knob configured to rotate the first tubular component relative to the housing. The shaft is fixed relative to a handle housing and thus does not rotate independent of the handle, even though the tubular components may rotate.

In an embodiment, the first mechanism includes an input gear in mesh with an internal gear of the knob, which is rotatable, such that rotation of the knob rotates the input gear. The first mechanism also includes a spline shaft having a transfer gear in mesh with the input gear such that rotation of the input gear causes rotation of the spline shaft. The spline shaft further includes a spline gear portion. The first mechanism further includes a drive shaft having an output gear (i.e., spur gear) in mesh with the spline gear portion of the spline shaft such that rotation of the spline shaft causes rotation of the drive shaft. The first tubular component is coupled to the drive shaft such that rotation of the drive shaft causes rotation of the first tubular component. In addition, in an embodiment, the second component is also coupled to the drive shaft so that the first and second components rotate together with the drive shaft. This rotation causes the preformed curvilinear section to also rotate, altering its orientation.

In an embodiment, the knob further includes an inner circumferentially-extending groove (i.e., on an inside diameter), and where the second mechanism further includes an input pin extending through an axially-extending slot in the housing. The pin is disposed in the groove of the knob wherein the pin bears against the walls of the groove to constrain axial movement of the knob independent of the pin. Thus, axial movement of the knob causes axial movement (i.e., a first linear movement) of the input pin. The knob, however, may be rotated without disturbing the axial position of the pin.

The second mechanism further includes a transmission and a shuttle. The transmission is coupled between the input pin and the shuttle, and is responsive to the first linear movement of the pin for causing a second linear movement of the shuttle. The shuttle, in turn, is configured to axially move the spur gear along the spline gear portion of the spline shaft. The axial movement of the spur gear, which is coupled to the drive shaft, operates to axially translate the drive shaft by the second linear movement. Since the second tubular component (i.e., the substantially "straight" component) is coupled to the drive shaft, they move axially together. The axial or linear movement adjusts the degree of deflection of the preformed curvilinear section.

In an embodiment, the transmission is further configured such that a transfer ratio of the second linear movement to the first linear movement is greater than or less than about one or unity, and may be much less than unity (e.g., 0.25:1, 0.33:1, 0.5:1 and the like) to about two or more than unity (e.g., 2:1, 3:1, 4:1, 5:1 and the like). Through the foregoing, relatively small linear movements of the knob result in relatively larger or lesser linear movements of the second tubular component, thus more easily adjusting the degree of deflection of the preformed curvilinear section.

The foregoing and other aspects, features, details, utilities, and advantages of embodiments of the present disclosure will be apparent to those of skill in the art from reviewing the following description and claims, and from reviewing the accompanying drawings.

BRIEF DESCRIPTION OF THE DRAWINGS

FIG. 1 is an isometric view of a catheter having omni-directional shaft deflection capability according to a first, handle-controlled embodiment.

FIG. 2 is a block diagram view of a catheter having omni-directional shaft deflection capability according to a second, robotic actuation-controlled embodiment.

DETAILED DESCRIPTION OF THE INVENTION

Figure 3:
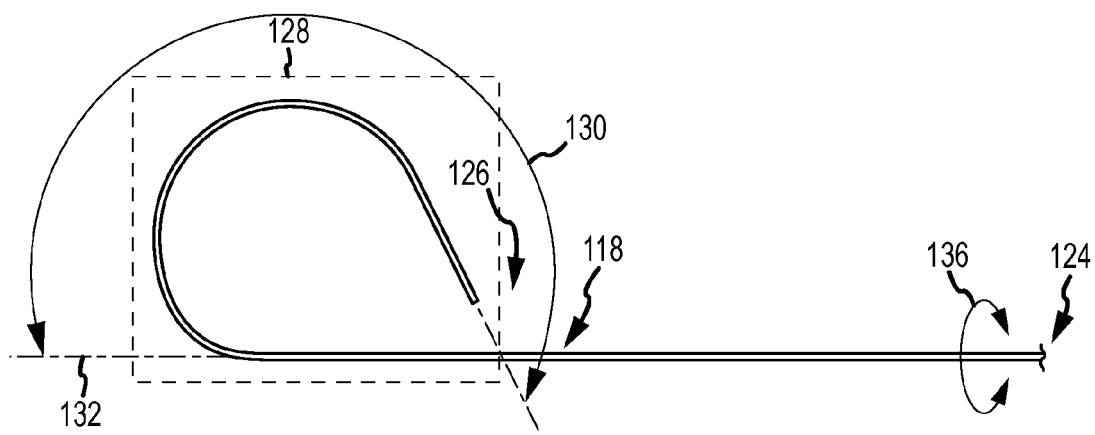
FIGS. 3-5 are respective side views of a shaft, an outer (substantially "straight") tubular component and an inner tubular component (with preformed curvilinear distal section) included in the shaft assembly of FIGS. 1-2.

Referring now to the drawings wherein like reference numerals are used to identify identical components in the various views, FIG. 1 shows a first, manually-actuated handle controlled embodiment of a catheter 100. The catheter 100 is configured for omni-directional deflection in three-dimensional space without steering or "pull" wire actuation. Catheter 100 may be an ablation catheter (i.e., either irrigated or non-irrigated), a sensing catheter (i.e., either electrode or non-electrode based), an electro-anatomical mapping catheter or other types of catheters now known or hereafter developed. Although not shown, catheter 100 may be configured for use with external electronics to facilitate such functionality, and may comprise, in the case of a mapping catheter, visualization, mapping and navigation/localization components known in the art, including among others, for example, an EnSite Velocity™ system running a version of NavX™ software commercially available from St. Jude Medical, Inc., of St. Paul, Minn. and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present invention, and hereby incorporated by reference in its entirety. Additionally, an electrophysiological (EP) monitor or display such as an electrogram signal display or other systems conventional in the art may also be coupled (directly or indirectly). Such an external localization system may comprise conventional apparatus known generally in the art, for example, an EnSite Velocity system described above or other known technologies for locating/navigating a catheter in space (and for visualization), including for example, the CARTO visualization and location system of Biosense Webster, Inc., (e.g., as exemplified by U.S. Pat. No. 6,690,963 entitled "System for Determining the Location and Orientation of an Invasive Medical Instrument" hereby incorporated by reference in its entirety), the AURORA® system of Northern Digital Inc., a magnetic field based localization system such as the gMPS system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties) or a hybrid magnetic field-impedance based system, such as the CARTO 3 visualization and location system of Biosense Webster, Inc. (e.g., as exemplified by U.S. Pat. No. 7,536,218, hereby incorporated by reference in its entirety). Some of the localization, navigation and/or visualization systems may involve providing a sensor for producing signals indicative of catheter location information, and may include, for example one or more electrodes in the case of an impedance-based localization system such as the EnSite™ Velocity system running NavX software, which electrodes may already exist in some instances, or alternatively, one or more coils (i.e., wire windings) configured to detect one or more characteristics of a low-strength magnetic field, for example, in the case of a magnetic-field based localization system such as the gMPS system using technology from MediGuide Ltd. described above.

In the case of ablation functionality, it should be understood that such ablation catheter systems may, and typically will, include other structures and functions omitted herein for clarity, such as such as one or more body surface electrodes (skin patches) for application onto the body of a patient (e.g., an RF dispersive indifferent electrode/patch for RF ablation), and at least one irrigation fluid source (gravity feed or pump), an RF ablation generator (e.g., such as a commercially available unit sold under the model number IBI-1500T RF Cardiac Ablation Generator, available from Irvine Biomedical, Inc) and the like.

With continued reference to FIG. 1, catheter 100 includes a shaft assembly 102 and a controller 104a. The shaft assembly 102 includes a proximal end portion 106 and a distal end portion 108. The controller 104a is configured, among other things, to control the shaft assembly 102 for omni-directional deflection in three-dimensional (3D) space. In FIG. 1, the distal end portion 108 is shown in a first, substantially straight state 110a as well as second, deflected state 110b (shown in dashed-line form).

In one embodiment, controller 104a is included in a user-actuatable handle 112 disposed at the proximal end of shaft assembly 102. Depending on the particular configuration of catheter 100 (e.g., an irrigated ablation catheter), handle 112 may be configured to facilitate the transport of irrigation fluid from an irrigation fluid source 114 to distal end portion 108. Handle 112 is configured to support typical clinician actuation inputs to effect omni-directional deflection, among other functions, as described and illustrated in greater detail below.

FIG. 2 is a block diagram of a second, robotically-actuated embodiment that includes shaft assembly 102, shown as a catheter 116. Catheter 116 may be the same as catheter 100 except that controller 104a (in the form a hand controller 112) has been replaced with a controller 104b, in the form of a robotically-actuated control system, for example, as seen by reference to U.S. application Ser. No. 12/751,843 filed Mar. 31, 2010 entitled ROBOTIC CATHETER SYSTEM, owned by the common assignee of the present invention and hereby incorporated by reference in its entirety. The robotically-actuated controller 104b is configured to manipulate and maneuver the catheter within a lumen or a cavity of a human body.

As described in the Background, conventional catheter shaft construction involves the use of metal pull wires wherein the catheter shaft is deflected by pulling on the wires. Repeated deflections of the catheter shaft in this manner may cause a compression (i.e., an axial foreshortening) of the catheter shaft at the distal end where the deflection occurs. The compression causes the catheter distal end to lose its original shape, dimensions and deflectability. Additionally, entanglements of the pull wires during catheter deflection are also known to occur, which limit the functionality and the operability of the catheter. The shaft assembly 102, as described below, overcomes these problems.

Figure 4:
Figure 5:
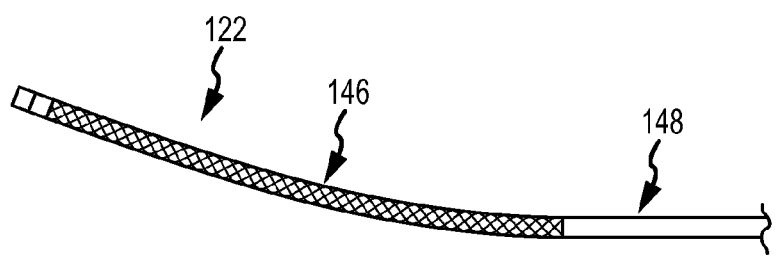

FIGS. 3-5 are side views of the individual components of shaft assembly 102, which includes a first tubular component 118 (FIG. 3), a second tubular component 120 (FIG. 4) and an outer shaft 122 (FIG. 5). The first tubular component 118 includes proximal and distal portions 124, 126, respectively, where proximal portion 124 has a substantially straight or linear section while the distal portion 126 includes a preformed curvilinear section, enclosed by dashed-line box 128 (hereinafter curvilinear section 128). Curvilinear section 128 may be configured to assume a wide range of preformed, fixed curves having differing amounts of deflection, the degree of deflection being indicated by a deflection angle 130. Section 128 has a predetermined resilience and thus a tendency to return to its preformed shape. Angle 130 extends between the distal free end of component 118 and a main longitudinal axis 132 component 118. In an embodiment, and for example only, angle 130 may be in the range greater between about zero (0) degrees and two-hundred seventy (270) degrees, preferably in the range of between about 90 and 270 degrees. It should be understood that curve shapes other than circular are contemplated, for example, an S-shape. Additionally, irregular shapes are contemplated for curvilinear section 128, as well as multiple revolution curves (e.g., multiple revolutions, such as 2, 3 or more).

In addition, component 118, more specifically curvilinear section 128, has a first stiffness or rigidity associated therewith that is lower than a second rigidity or stiffness associated with second tubular component 120. This rigidity difference allows curvilinear section 128 to be progressively deformed by second tubular component 120 away from its preformed curve to a lesser angle 130, to about zero degrees (i.e., straight).

In an embodiment, component 118 further includes an inner lumen 134 (best shown in FIG. 6) configured, for example, for the transport of irrigation fluid. Controller 104*a* (or 104*b*) is configured to rotate component 118 about axis 132 to cause curvilinear section 128 to sweep through three-dimensional space. Component 118 may comprise conventional biocompatible materials capable of being preformed into the desired curvilinear shape and further being capable of repeated elastic deformation (i.e., capable of sustaining relatively large elastic strains in view of the contemplated range of deflection). In an embodiment, component 118 may comprise such materials as shape memory alloys (SMA), including metal materials such as stainless steel or nickel titanium alloys (e.g., superelastic NITINOL).

Referring to FIG. 4, second tubular component 120 is substantially straight and hence is also referred to sometimes herein as a "second straight component" or a "straight component" and has a longitudinal axis 138. The term "straight" is meant to include substantially or relatively straight in relation to curvilinear section 128 of component 118. The straight component 120 maintains its relative rigidity (and straightness) through the operation and movement of catheter 100. Straight component 120 further includes an central lumen 140 (best shown in FIG. 6) extending between proximal and distal ends. The central lumen 140 is configured in size and shape to accommodate radially inner component 118 in a concentric and slidably movable relationship. As shown in FIG. 4, controller 104*a* (or 104*b*) is configured to move straight component 120 in both a longitudinal direction, shown by reference numeral 142 and in a rotational direction, shown by reference numeral 144. Straight component 120 may comprise conventional biocompatible materials, for example, metal materials such as stainless steel or nickel titanium alloys (e.g., superelastic NITINOL). As mentioned above, straight component 120 is more rigid than curvilinear section 128. Components 118, 120 may also comprise any suitable biocompatible polymer material known in the art of medical instruments, such as engineered nylon resins and plastics, and in such embodiments, the second component 120 may be fabricated with a relatively high durometer (Shore) material, with respect to the first component 118, so that the second component 120 can "control" the first component as described (and depicted).

In alternate embodiments, both first and second tubular components 118, 120 may comprise not only substantially continuous structures (e.g., such as a tube, as described and illustrated), but may also comprise a discrete structure (e.g., such as a spiral coil, a mesh or a braid) or a discrete structure embedded within a continuous structure (e.g., such as a reinforced shaft). In still further embodiments, components 118, 120 may each alternately comprise segmented components wherein each of the multiple segments have differing/varying physical properties (e.g., shape, structure, dimension, stiffness, thermal conductivity, electrical conductivity as well as chemical properties such as material composition).

Referring to FIG. 5, outer shaft 122 includes proximal and distal ends substantially aligned with proximal and distal end portions 106, 108 of shaft assembly 102 overall. Shaft 122 may include a relatively flexible distal segment 146 and a relatively less flexible proximal segment 148. Shaft 122 includes a central lumen 150 (best shown in FIG. 6) configured in size and shape to accommodate the radially-inwardly disposed first and second components 118, 120, and to allow either or both of components 118, 120 to slidably move with respect to shaft 122. Shaft 122 may be fabricated according to known processes, such as multilayer processing including extrusion processes, mandrel-based processes and combinations thereof from any suitable biocompatible polymer material known in the art of medical instruments, such as engineered nylon resins and plastics, including but not limited an elastomer commercially available under the trade designation PEBAX® from Arkema, Inc. of a suitable durometer, melting temperature and/or other characteristics. In this regard, shaft 122 is characterized with a rigidity that is less than that associated with the preformed curvilinear section 128, such that shaft 122 will adapt or otherwise conform to the shape of curvilinear section 128 (in the absence of straight component 120).

In one embodiment, relatively flexible segment 146 comprises material that provides greater flexibility than the proximal segment 148. For example only, shaft 122 (other than in relatively flexible segment 146) may comprise PEBAX® material having a hardness/rigidity within a range of between about 60-75D (durometer), and may be about 72D (durometer) hardness and include braided material for kink reduction. Flexible segment 146 may be PEBAX® material with a durometer generally in the range of between about 22-50D and may be 25D, 35D or 40D hardness (i.e., more flexible).

It should be understood that variations in the size and shape of first tubular component 118 are contemplated that are adequate to support all applicable uses. It is recognized that based on the application and/or use of catheter 100, the length of first tubular component 118 may vary. In an embodiment, the length of curvilinear section 128 may range from approximately 1.5 inches to approximately 6 inches in length, and may be about 2 inches (10 cm). Likewise, the diameter of shaft assembly 102 may vary depending upon the particular application, although generally shaft assembly 102 (i.e., the outside diameter of the shaft 122) may range between 4-7F (French) in size. In an embodiment, shaft 122 may be 5F (French) in size. In a further embodiment, shaft 122 may include a 7F flare at distal end portion 108, which may be configured for a press-fit connection with an ablation tip assembly in an ablation catheter embodiment (best shown in FIG. 16).

Figure 6:
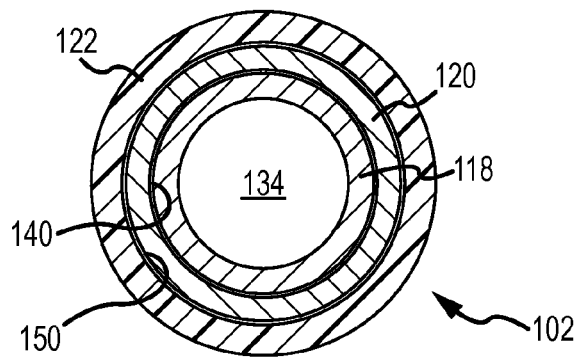
FIG. 6 is a cross-sectional view of the shaft assembly of FIG. 1 taken substantially along lines 6-6.

FIG. 6 is a cross-sectional view of shaft assembly 102 of FIG. 1 taken substantially along lines 6-6. The first and second components 118, 120 and outer shaft 122 are disposed generally in a concentric relationship. The outside diameter of first component 118 and the inside diameter of straight component 120 are selected so as to form a relatively small intervening clearance therebetween to allow for slidable relative movement. More specifically, the slidable movement allows the distal end of straight component 120 to slide and bear against curvilinear section 128. Inner lumen 150 of shaft 122 is configured to accommodate both first and second components 118, 120. In other words, the diameter of lumen 150 is slightly greater than the outside diameter of straight component 120 so as to form another small intervening clearance therebetween, which allows for slidable movement of the straight component 120 relative to shaft 122, rotational movement of straight component 120 relative to shaft 122 as well as for electrical conductors to extend the length between proximal and distal ends of the catheter shaft assembly so as to permit electrical connections between handle 112 and electrical/electronic components (e.g., electrodes, sensors, etc.) at the catheter distal end.

In the illustrated embodiment, first component 118 is received within lumen 140 in a first concentric relationship, with component 118 being radially-inwardly disposed relative to straight component 120. In an alternate embodiment (not shown), straight component 120 is received within a central lumen (not shown) of first component 118 in a second, different concentric relationship. In the second concentric relationship, component 118 is disposed outside of straight component 120. However, in such a second concentric relationship, lumen 134 previously described above as being available for carrying irrigation fluid is no longer available for such purpose.

Figure 7:
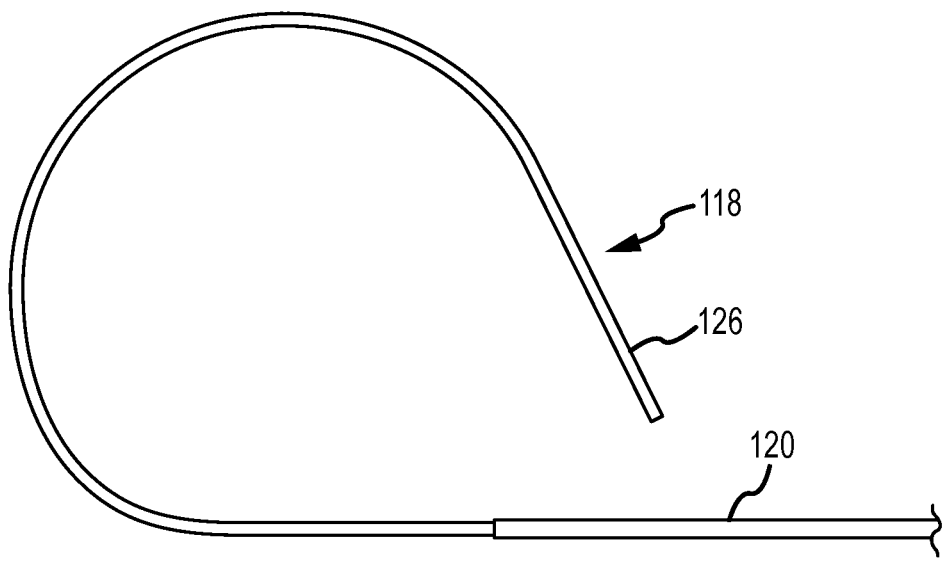
FIGS. 7-8 show the shaft assembly of FIGS. 1-2 in different stages of manufacture.
Figure 8:
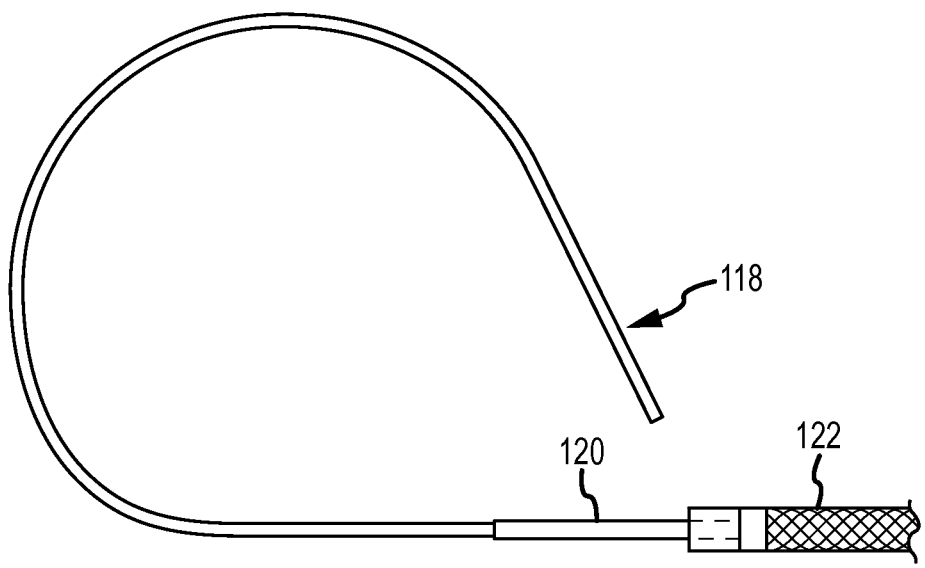

FIGS. 7-8 are side views of shaft assembly 102 of catheter 100, shown in different stages of manufacture. Referring to FIG. 7, the first step in a method of manufacture involves assembly of first component 118 and straight component 120. In this regard, straight component 120 has lumen 140 (best shown in FIG. 6) that extends between proximal and distal ends. The size (i.e. diameter) of lumen 140 is larger than the external cross-sectional dimension (i.e., outside diameter) of first component 118. The proximal end (not shown in FIG. 7) of first component 118 is inserted into lumen 140 at the distal end of straight component 120. In the first concentric relationship, first component 118 is configured as a radially inner tubular component of shaft assembly 102 while second (straight) tubular component 120 is configured as a radially intermediate component of shaft assembly 102. In the second concentric relationship described above, however, the positions are switched, with the distal end of straight component 120 being first inserted into the central lumen (not shown) of component 118 at the proximal end of component 118. In this alternate embodiment, second (straight) component 120 is configured as a radially inner component of shaft assembly 102 while first (curved end) component 118 is configured as a radially intermediate tubular component.

Referring now to FIG. 8, the next step of the method of manufacture involves the inclusion of shaft 122. In particular, the proximal ends of component 118, 120 are inserted into central lumen 150 of shaft 122 at its distal end. This is shown in FIG. 8. Once shaft assembly 102 has been assembled, proximal end 106 may be connected to controller 104a (or 104b) for omni-directional deflection without the use of pull wires, without suffering from the ill effects of shaft compression (i.e., axial foreshortening of the distal end portion) or without rotation of outer shaft 122. In an alternative embodiment, an ablation tip (electrode) may be coupled to the distal end of shaft assembly 102, as will be described below in connection with FIG. 16.

FIGS. 9-14 are views of catheter 100 showing a method of deflecting the distal end, in various degrees, in a single plane. The degree or angle of deflection (i.e., angle 130) may be adjusted (in a single plane) by (1) linear displacement of second (straight) component 120 relative to first (curved end) component 118; (2) linear displacement of first (curved end) component 118 relative to second (straight) component 120; or (3) a combination of linear displacements of both first (curved end) component 118 and second (straight) component 120 so as to effect a net linear, relative displacement therebetween. A common characteristic of the foregoing displacement modes is that each mode involves altering the axial position of the distal end of the straight component 120 on the curvilinear section 128.

To accomplish either of the first or second displacement modes noted above, a single linear displacement mechanism may be incorporated into controller 104a (or 104b). To accomplish the third displacement mode, however, a pair of mechanisms (i.e., first and second linear displacement mechanisms) may be coupled to the proximal ends of components 118, 120. As described below, a handle controller 112 may be configured to achieve a linear displacement of the straight component 120 relative to component 118.

Figure 9:
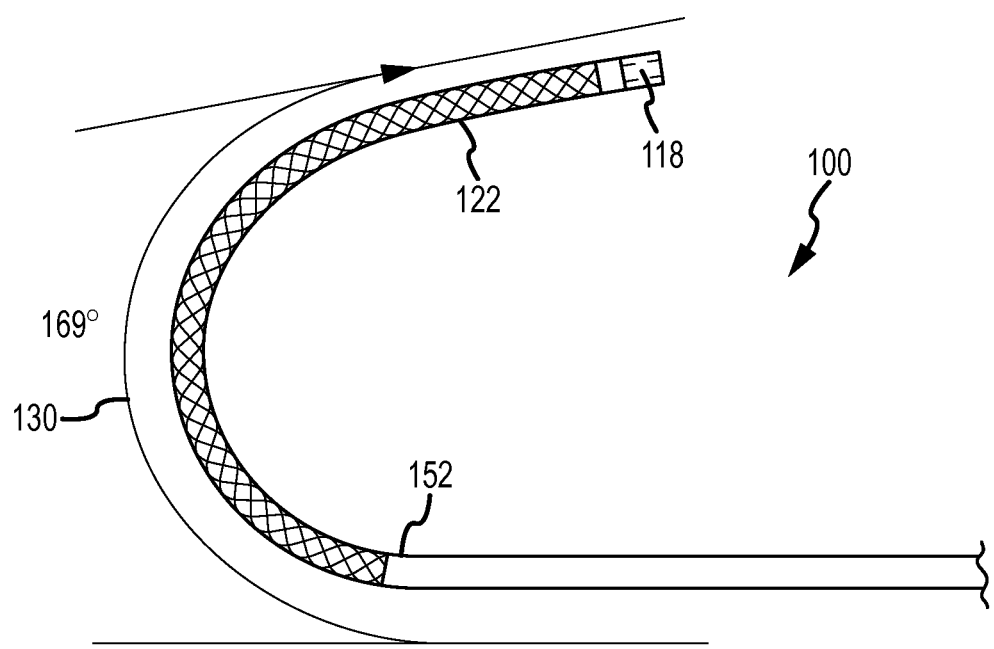
FIGS. 9-14 show the shaft assembly of FIGS. 1-2 in different degrees of deflection.

FIG. 9 shows a deflection angle 130 of about 169°. Radially inward component 118 is shown at the distal end of shaft 122. In FIG. 9, the distal end of straight component (not shown) does not extend in the distal direction beyond about axial point 152 (i.e., visually—where the straight portion of catheter 100 transitions into the curved portion of catheter 100).

Figure 10:
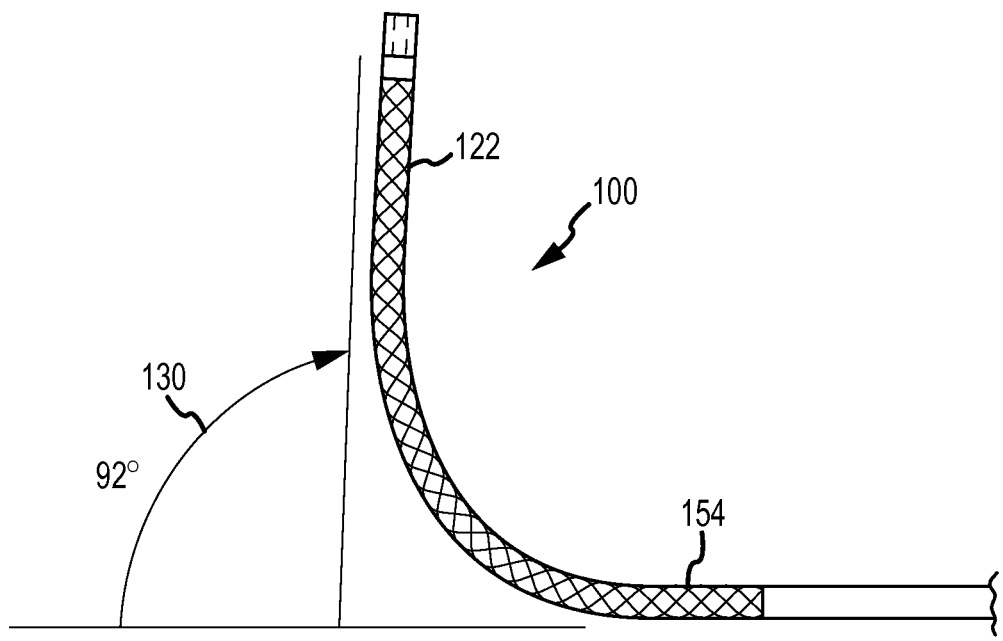

FIG. 10 shows a deflection angle 130 of about 92°. In FIG. 10, the distal end of the second (straight) component (not shown) does not extend in the distal direction beyond about axial point 154 (i.e., visually—where the straight portion of catheter 100 transitions into the curved portion of catheter 100).

Figure 11:
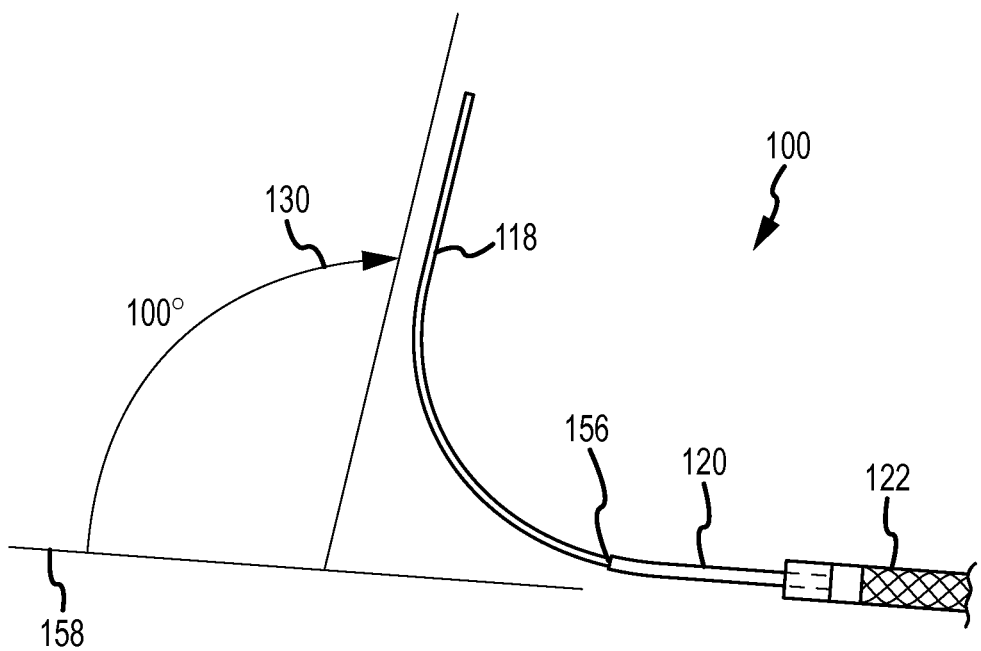

FIG. 11 is similar to FIG. 10 but with outer shaft 122 withdrawn (i.e., moved toward to the proximal end) to reveal inner components 118, 120. FIG. 11 shows a deflection angle 130 of curvilinear section 128 to be about 100°. The distal end of the second (straight) component 120 extends in the distal direction to about axial point 156 (i.e., visually—where the straight portion of catheter 100 transitions into the curved portion of catheter 100). As the distal end of straight component 120 is slid in the distal direction, straight component 120, being more rigid, progressively deflects the preformed curvilinear section towards main longitudinal axis 158. The amount the curvilinear section deflects from its preformed shape corresponds to the axial position of the distal end of straight component 120 relative to preformed curvilinear section 128. On the other hand, when the distal end of straight component 120 is moved in an opposite direction (i.e., in a direction towards the proximal end), the distal end of straight component 120 progressively changes its position along the curvilinear section, thereby progressively allowing the curvilinear section to return to its full preformed shape.

Figure 12:
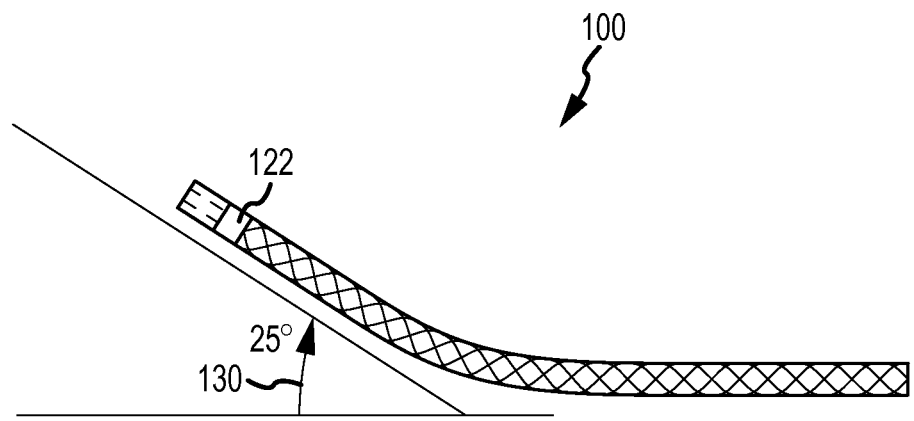
Figure 13:
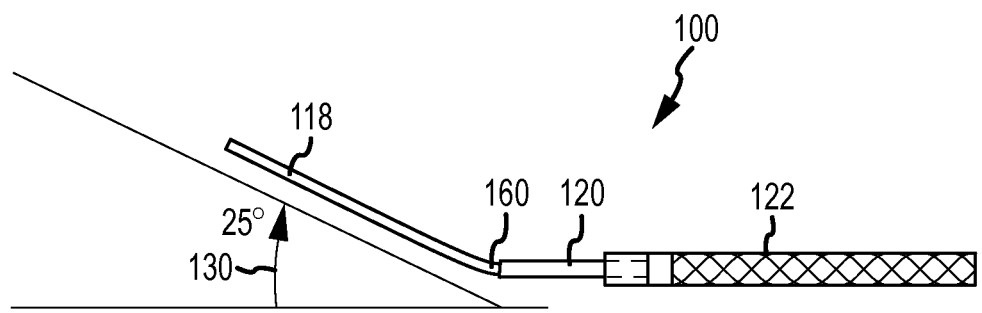

FIGS. 12-13 show catheter 100 from the previous FIGS. 9-11, with the exception that straight component 120 has been linearly displaced in the distal direction to about axial point 160 (best shown in FIG. 13). In FIGS. 12-13, deflection angle 130 is about 25°. In FIG. 13, shaft 122 has been withdrawn to better show the relative positions of components 118, 120.

Figure 14:
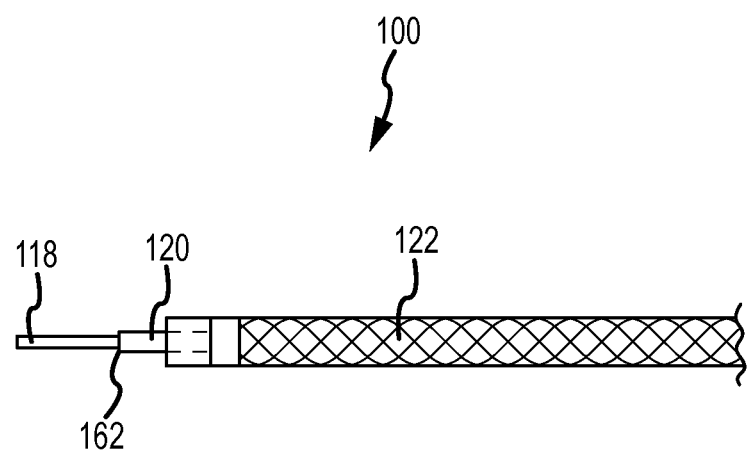

FIG. 14 shows catheter 100 from the previous FIGS. 9-13, with the exception that straight component 120 has been linearly advanced (extended) in the distal direction such that the distal end is positioned at about axial point 162. In FIG. 14, deflection angle is about zero degrees (0°) or in other words "straight". Through the foregoing, distal catheter tip bending may be accomplished without the use of steering wires, without rotating the outer shaft and without any associated shaft compression.

FIGS. 15A-15F show catheter 100 as the subject of a method of moving a catheter tip, including curvilinear section 128, to a plurality of different orientations. In FIGS. 15A-15F, the distal end portion of catheter 100 has a deflection angle of over 150 degrees. Based on the shaft structure described above, changes in orientation of catheter 100 may be accomplished by (1) rotating the first (curved end) component 118; (2) rotating the second (straight) component 120; or (2) rotating both the first and second components 118, 120 so as to effect a net rotation of the first (curved end) component 118. First and (if used) second rotation mechanisms may be incorporated into hand controller 112 and may be coupled to the components 118, 120 at their respective proximal ends. Alternatively, as described in connection with FIG. 2, a robotically-actuated controller 104b may be used in lieu of (or in combination with) controller 104a (handle 112). As a further alternative, certain aspects of handle 112 may be implemented using electro-mechanical means.

Figure 15:
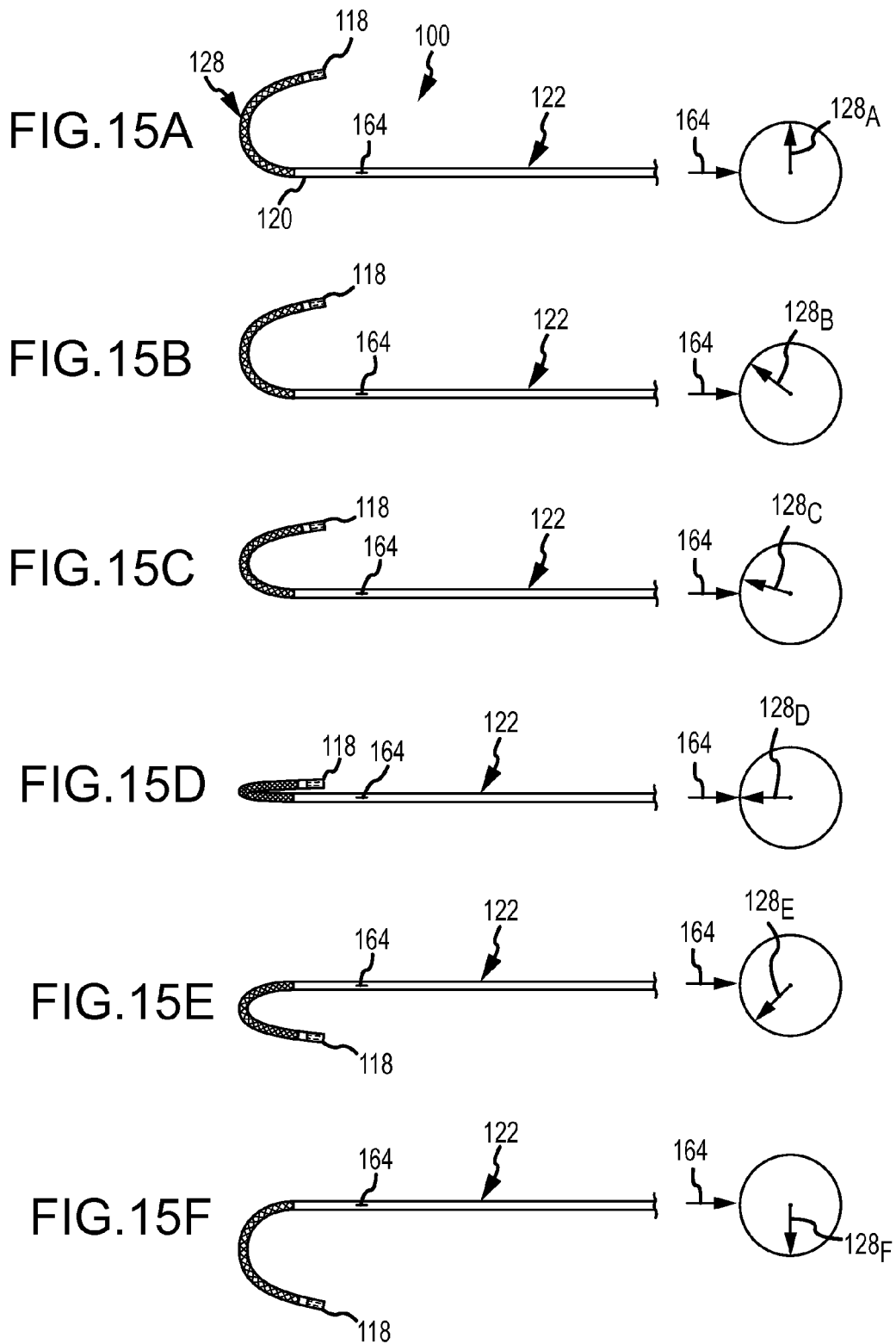
FIGS. 15A-15F show rotation of the catheter distal end portion, while in a deflected condition, without a corresponding rotation of the outer shaft.

FIG. 15A shows catheter 100 in an initial starting orientation, which will be referred to as a zero degree orientation (i.e., section 128 lies in the plane of the paper). For reference, indicia 164 is shown on outer shaft 122 to demonstrate that shaft 122 does not rotate during these maneuvers. In other words, a shaft orientation of shaft 122 remains in a fixed rotational position. The preformed curvilinear section 128 is also shown.

FIG. 15B shows catheter 100 in a second orientation where a plane through section 128 makes about a 30 degree angle with the plane of the paper. The illustrated change in orientation is made by rotating one or both of first component 118 and/or second component 120. Note that indicia 164 does not reveal any rotation of shaft 122.

FIG. 15C shows catheter 100 in a third orientation where a plane through section 128 makes about a 60 degree angle with the plane of the paper. Again, indicia 164 indicates that shaft 122 does not rotate.

FIG. 15D shows catheter 100 in a fourth orientation where a plane through section 128 makes about a 90 degree angle with the plane of the paper. Indicia 164 indicates that shaft 122 does not rotate.

FIG. 15E shows catheter 100 in a fifth orientation where a plane through section 128 makes about a 135 degree angle with the plane of the paper. Indicia 164 indicates that shaft 122 does not rotate.

FIG. 15F shows catheter 100 in a sixth orientation where a plane through section 128 makes about a 180 degree (or zero degree) angle with the plane of the paper. Indicia 164 indicates that shaft 122 does not rotate. It should be understood that the foregoing sequence can be extended to encompass 360 degrees. Moreover, when combined with the adjustment of deflection angle 130 described above, embodiments of the invention provide a catheter construction and control mechanism to accomplish omni-directional deflection capability.

FIGS. 15A-15F also include respective clock face diagrams to further demonstrate that while the outer shaft 122 does not rotate, the inner components 118, 120 do rotate. In the clock face diagrams, indicia 164 is located on shaft 122 at approximately a twelve o'clock position in FIG. 15A, which position does not change throughout the remainder of FIGS. 15B-15F, indicating no rotation. However, curvilinear section 128, which is designated as $128_A$ in FIG. 15A, is initially at about a three o'clock position, but thereafter rotates counterclockwise, assuming positions $128_B$, $128_C$, $128_D$, $128_E$ and $128_F$ in FIGS. 15B-15F, respectively.

Figure 16:
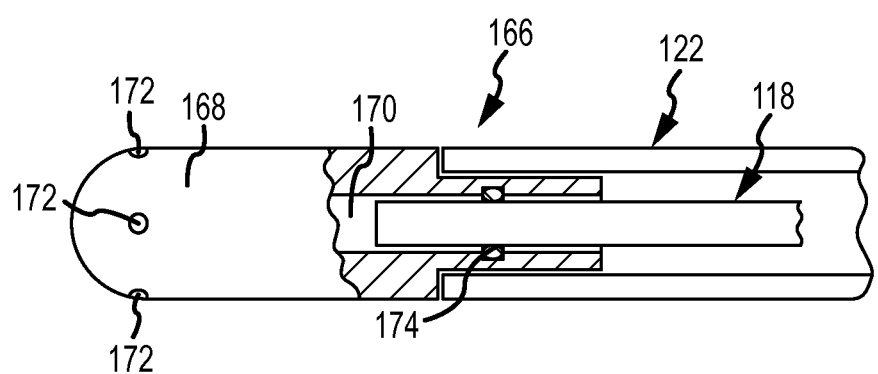
FIG. 16 is a cross-sectional side view, with portions broken away, showing an irrigated ablation tip configured with an O-ring seal suitable for connection to the distal end of the shaft assembly of the catheter of FIGS. 1-2.

FIG. 16 shows an exemplary ablation tip electrode 166 suitable for use in connection with catheter 100. Electrode 166 has a main electrode body 168 of electrically-conductive material and includes an ablation surface, which may be smooth with cylindrical and hemispherical portions, and an irrigation fluid manifold 170 internal to electrode 166 configured to deliver irrigation fluid (e.g., saline) to one or more irrigation ports 172. The manifold 170 includes an inlet that is configured with an O-ring seal 174 or the like. O-ring seal 174 is configured in size and shape to make a tight, leak proof seal with the outside diameter surface of first tubular component 118. In this embodiment, component 118 includes a central lumen (e.g., lumen 134 in FIG. 6) configured to carry irrigation fluid from source 114 to manifold 170. The O-ring seal 174 allows component 118 to rotate (e.g., as described above) relative to the electrode 166. Note that shaft 122 is coupled to electrode 166 by press-fitting shaft 122 over and onto a proximal shank portion of electrode 166. Accordingly, since shaft 122 does not rotate (i.e., relative to handle 112), neither will the electrode 166. Thus, the O-ring seal 174 allows for the above-describe relative rotation. In other respects, electrode 166 may comprise conventional construction techniques and materials. Examples of suitable, electrically conductive materials include (but are not limited to) gold, platinum, iridium, palladium, copper, nickel, stainless steel, and various mixtures, alloys and combinations thereof.

With continued reference to FIG. 16, it should be understood that catheter 100, for example, the relatively flexible distal segment 146 (best shown in FIG. 5) of shaft 122, may be further configured to carry various electrodes, sensors and transducers configured to transfer, receive or sense energy to and from an environment external or internal thereto.

Figure 17:
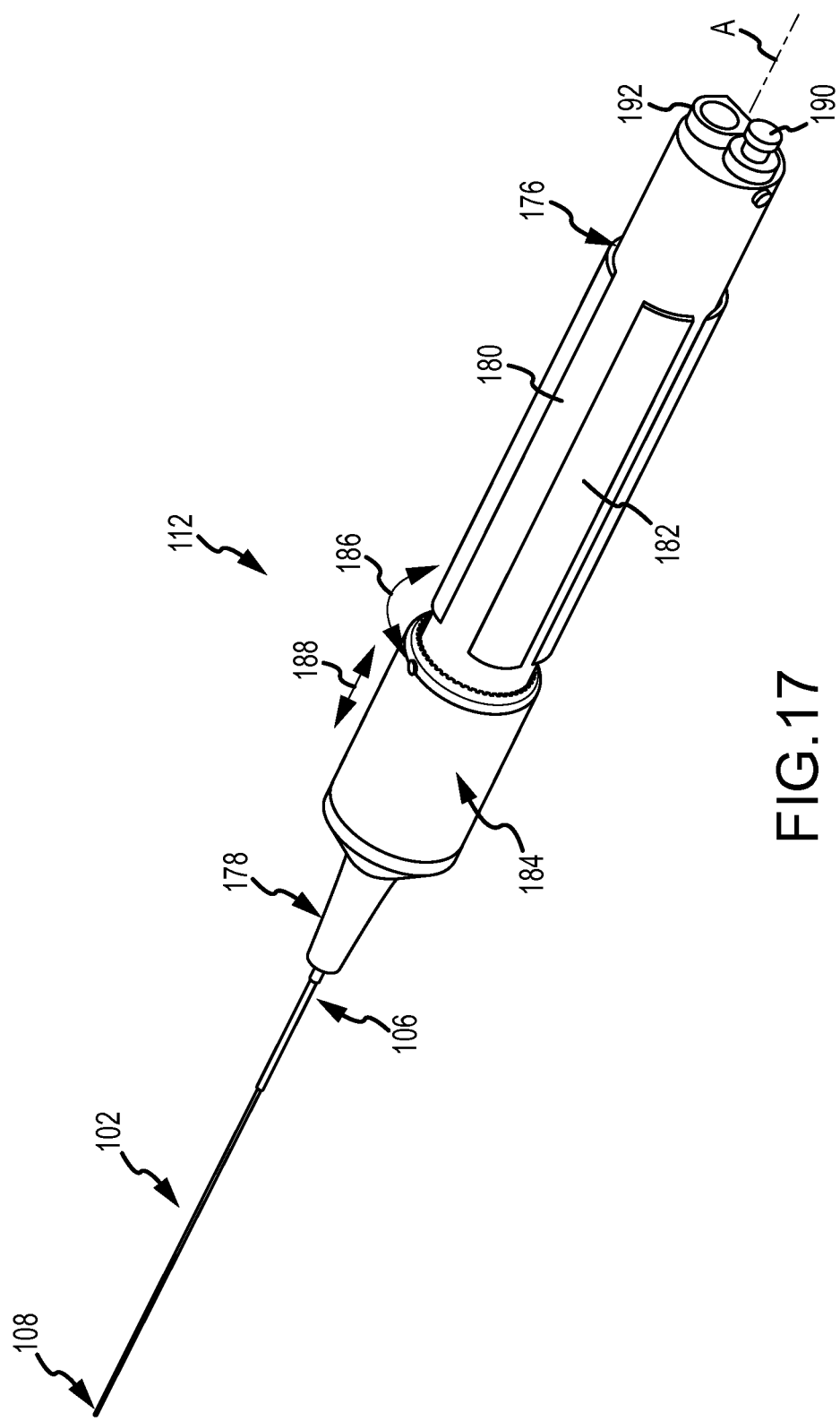
FIG. 17 is an enlarged isometric view of the handle of FIG. 1.

FIG. 17 is an isometric view showing, in an enlarged fashion, handle controller 112 of FIG. 1. Handle 112 is configured with a first mechanism or means for imparting a rotation to first and second components 118, 120 so as to alter an orientation of curved section 128. Handle 112 is also configured with a second mechanism or means for imparting a linear displacement to second component 120 relative to first component 118 so as to alter the curvilinear shape of section 128. Handle 112 is disposed at the proximal end 106 of shaft assembly 102.

Handle 112 includes, generally, a housing 176 with a strain relief member 178, a grip area 180 including lands 182, a user-actuatable knob 184 configured for rotational movement 186 as well as linear (axial) movement 188, an irrigation fluid inlet 190 and an electronic/electrical connector or coupler 192.

Housing 176 is configured generally to contain, isolate and protect the inner components from external influences. Housing 176 is generally cylindrical in shape extending along a longitudinal axis "A". Housing 176 may comprise conventional materials, such as engineered nylon resins and plastics, including but not limited an elastomer commercially available under the trade designation PEBAX® from Arkema, Inc., and various biocompatible metals, such as stainless steel, aluminum and the like.

Strain relief member 178 is configured to provide a mechanical interface between handle 112 and shaft assembly 102. As described in greater detail below, outer shaft 122 of the shaft assembly 102 may be fixed to handle 112 via fixation to strain relief member 178.

Grip area 180 is configured in size and shape to be gripped by a user's hand for manual actuation of knob 184. The grip area 180 may optionally include lands 182 formed of relatively soft (i.e., low durometer) material, such as silicone or the like, configured to reduce slip and ensure a comfortable grip (e.g., for extended medical procedures).

Figure 18:
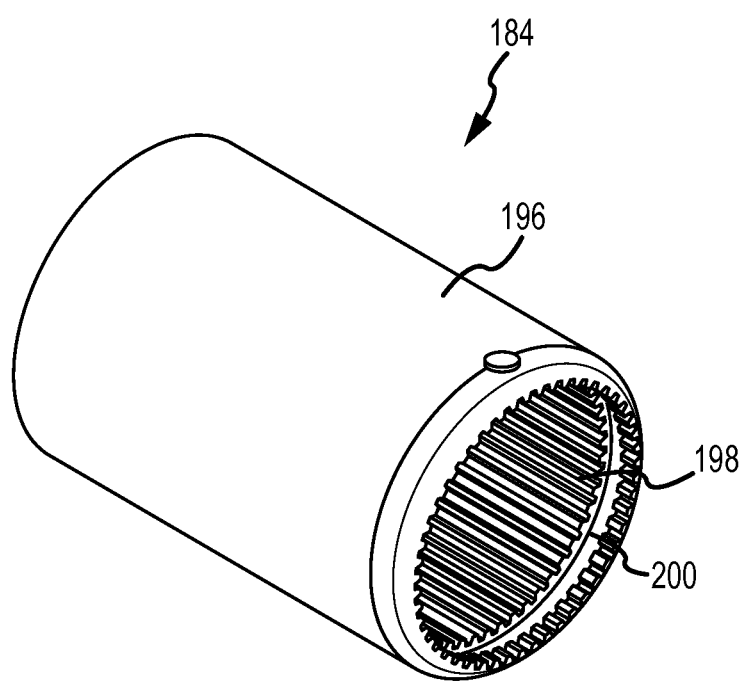
FIG. 18 is an isometric view of a knob portion of the handle of FIG. 17.

FIG. 18 is an isometric, enlarged view of knob 184. Knob 184 comprises an elongate ring disposed outside of (i.e., radially outwardly of) a cylindrical portion 194 (best shown in FIG. 19) of housing 176. Knob 184 has an outer surface 196 that may be smooth (as shown) or may contain surface features to enhance a user's grip. Knob 184 includes an internal gear 198, comprising a plurality of radially-inwardly facing teeth, on an inner circumference thereof. Knob 184 further includes an inner circumferentially-extending groove 200 at an axial end thereof. Knob 184 may comprise conventional materials (i.e., the same as described for housing 176) and manufactured using conventional construction techniques.

Referring again to FIG. 17, knob 184 is configured for bi-directional rotation as indicated by double arrow-headed line 186 (i.e., both clockwise and counter-clockwise). In the illustrated embodiment, when knob 184 is rotated, first (curved end) component 118 and second (straight) component 120 also rotate but shaft 122 does not rotate. The rotation alters the orientation of curvilinear section 128 (i.e., as in FIGS. 15A-15F). In addition, knob 184 is configured for bi-directional linear movements, such as back and forth movements in the directions of double arrow-headed line 188. Movement of knob 184 in a linear direction 188 translates second (straight) component 120 relative to the first (curved end) component 118, changing the angle of deflection, as also described above (i.e., as in FIGS. 9-14). Through the foregoing rotational and linear actuation of knob 184, a user may manually manipulate catheter 100 in the manner described above.

Irrigation inlet 190 is configured to receive, in irrigated ablation catheter embodiments, irrigation fluid from a source (e.g., source 114—best shown in FIG. 1). Connector 192 is configured as an electrical or electronic interface for catheter 112. For example, connector 192 may be configured for connection to an RF ablation generator in RF ablation embodiments, positioning/navigation systems as described above or the like.

Figure 19:
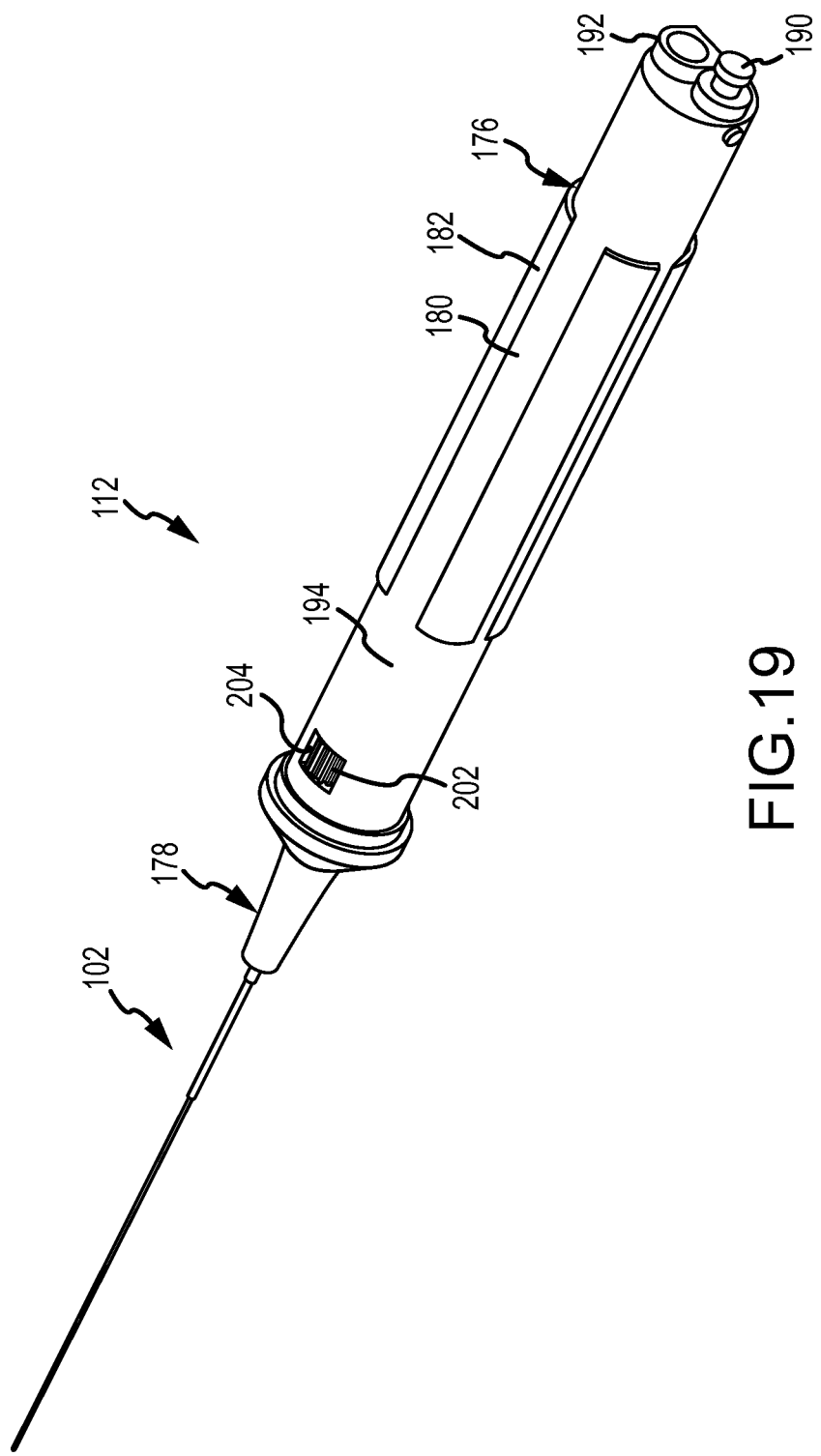
FIG. 19 is a top isometric view of the handle of FIG. 17 with the knob omitted, showing an input gear for rotational input.

FIG. 19 is an isometric view of handle 112 of FIG. 17 except that knob 184 has been omitted for clarity and to reveal an input gear 202 extending through an opening 204 in housing 176. Input gear 202 is in mesh with internal gear 198 of knob 184 such that rotation of knob 184 causes a corresponding rotation of input gear 202. Input gear 202 is thus configured to receive a rotational input from knob 184 and to transfer such rotational input to the internal rotational mechanism of handle 112, which will be described below. For reference purposes only, FIG. 19 is a top view of handle 112.

Figure 20:
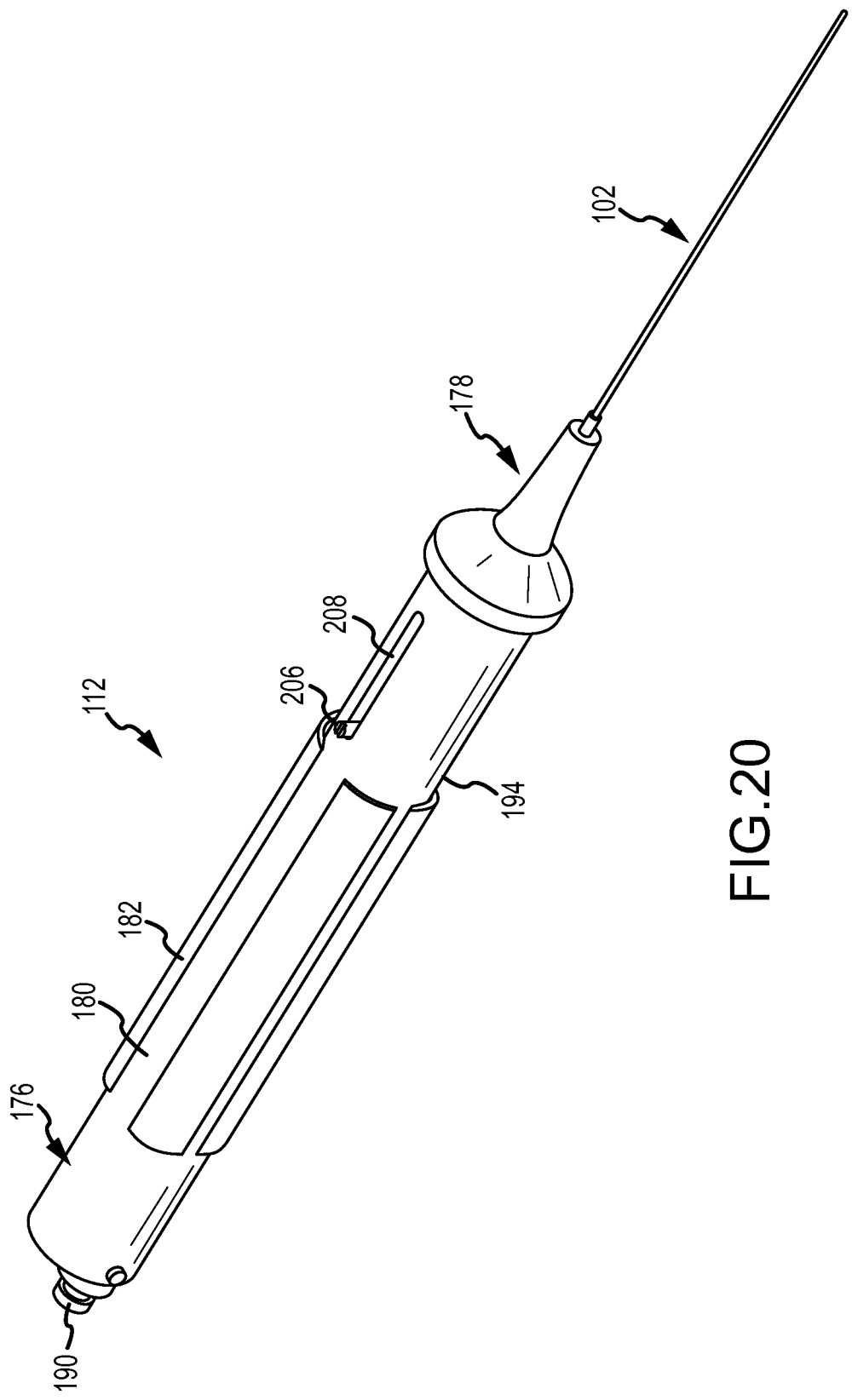
FIG. 20 is a bottom isometric view of the handle of FIG. 17 with the knob omitted, showing an input pin for axial input.

FIG. 20 is an isometric view of handle 112 of FIG. 17 except that knob 184 has been omitted for clarity and is of the bottom of handle 112, opposite the side shown in FIG. 19. Omitting knob 184 in FIG. 20 reveals an input pin 206 projecting through an axially-extending slot 208 in housing 176. The input pin 206 is configured to be seated in groove 200 of knob 184 when knob 184 is mounted on cylindrical portion 194 of housing 176. The pin 206 bears against the walls of groove 200, thereby constraining free axial movement of knob 184. Thus, axial movement of knob 184 causes a corresponding axial movement of pin 206 (hereinafter a first linear movement of input pin 206). The pin/groove arrangement, however, permits rotation of knob 184 without altering the axial position of input pin 206. Thus, knob 184, input gear 202 and input pin 206 cooperate to permit manually-actuated rotational and linear movements to be captured as inputs to be provided to the internal mechanisms of handle 112 (more below) for controlling the deflection angle and orientation of curvilinear section 128.

Figure 21:
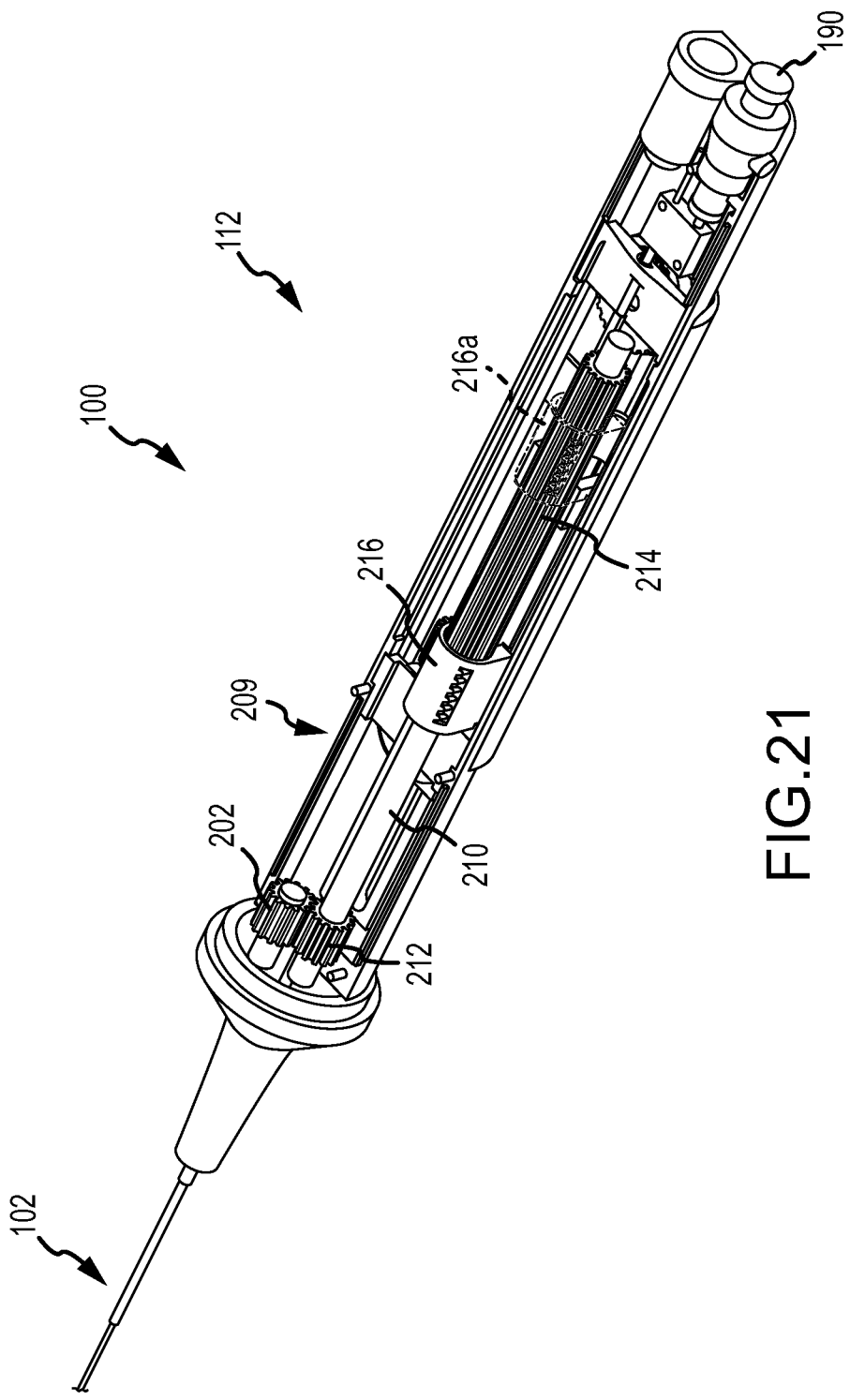
FIG. 21 is an isometric view of the handle of FIG. 17 with a top portion of the housing omitted.

FIG. 21 is an isometric view of handle 112 with a top portion of housing 176 removed to show the internal components thereof. A first mechanism 209 is shown that is responsive to a rotational input from input gear 202 to effect a rotational displacement of first component 118. First mechanism 209 includes a spline shaft 210 having a transfer gear 212 and a spline gear portion 214. Mechanism 209 further includes a shuttle 216 to facilitate linear displacement of straight component 120 but that is also configured for linear movement along spline shaft 210, maintaining a spur gear 220 (shown in FIG. 23) in mesh with spline gear portion 214. To illustrate the movement of shuttle 216, FIG. 21 also shows the shuttle in an exemplary, alternate position, shown as shuttle 216a (in dashed line form).

Figure 22:
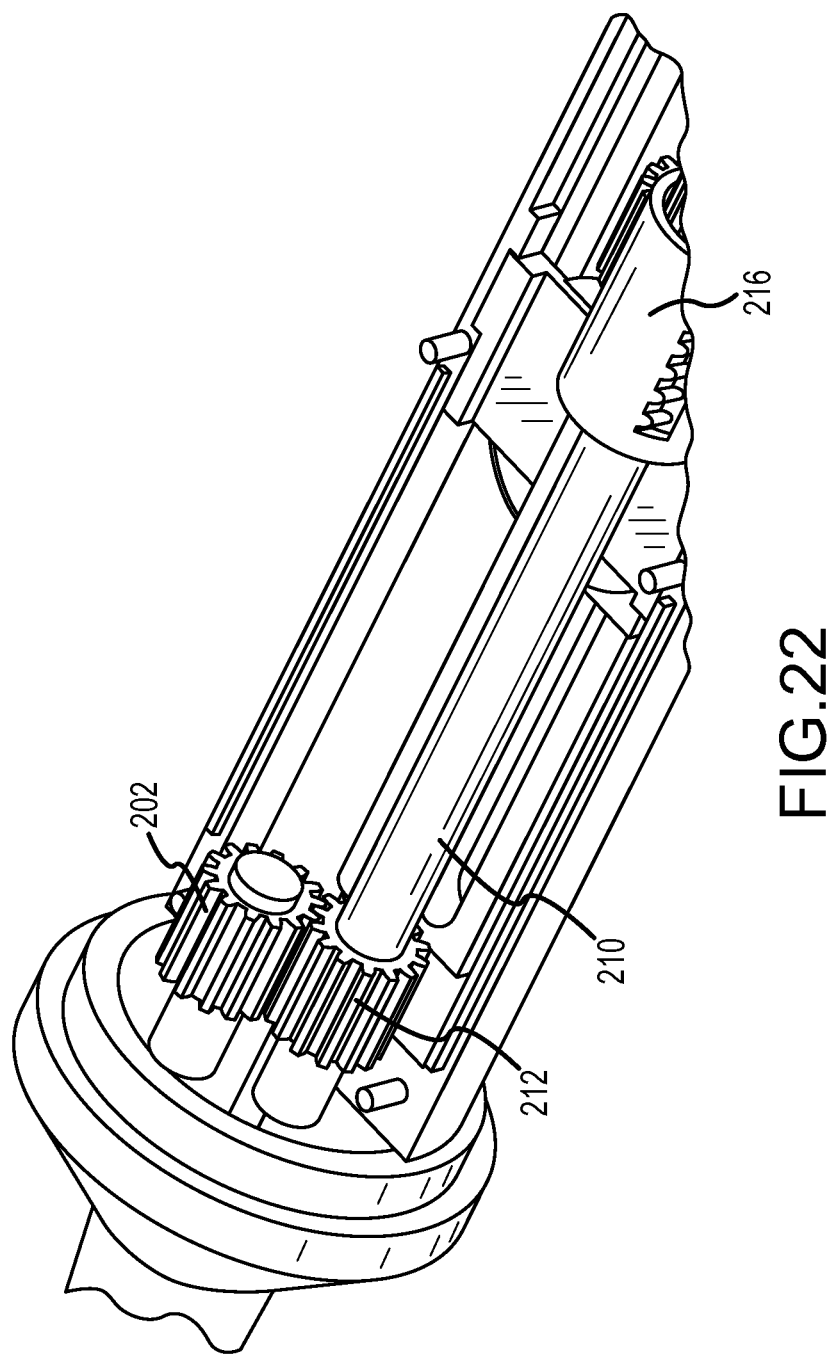
FIG. 22 is an enlarged isometric view of FIG. 21.

FIG. 22 is an enlarged isometric view of handle 112. Input gear 202 is in mesh with transfer gear 212. Accordingly, rotation of input gear 202 causes a corresponding rotation of transfer gear 212 and thus also rotation of spline shaft 210.

Figure 23:
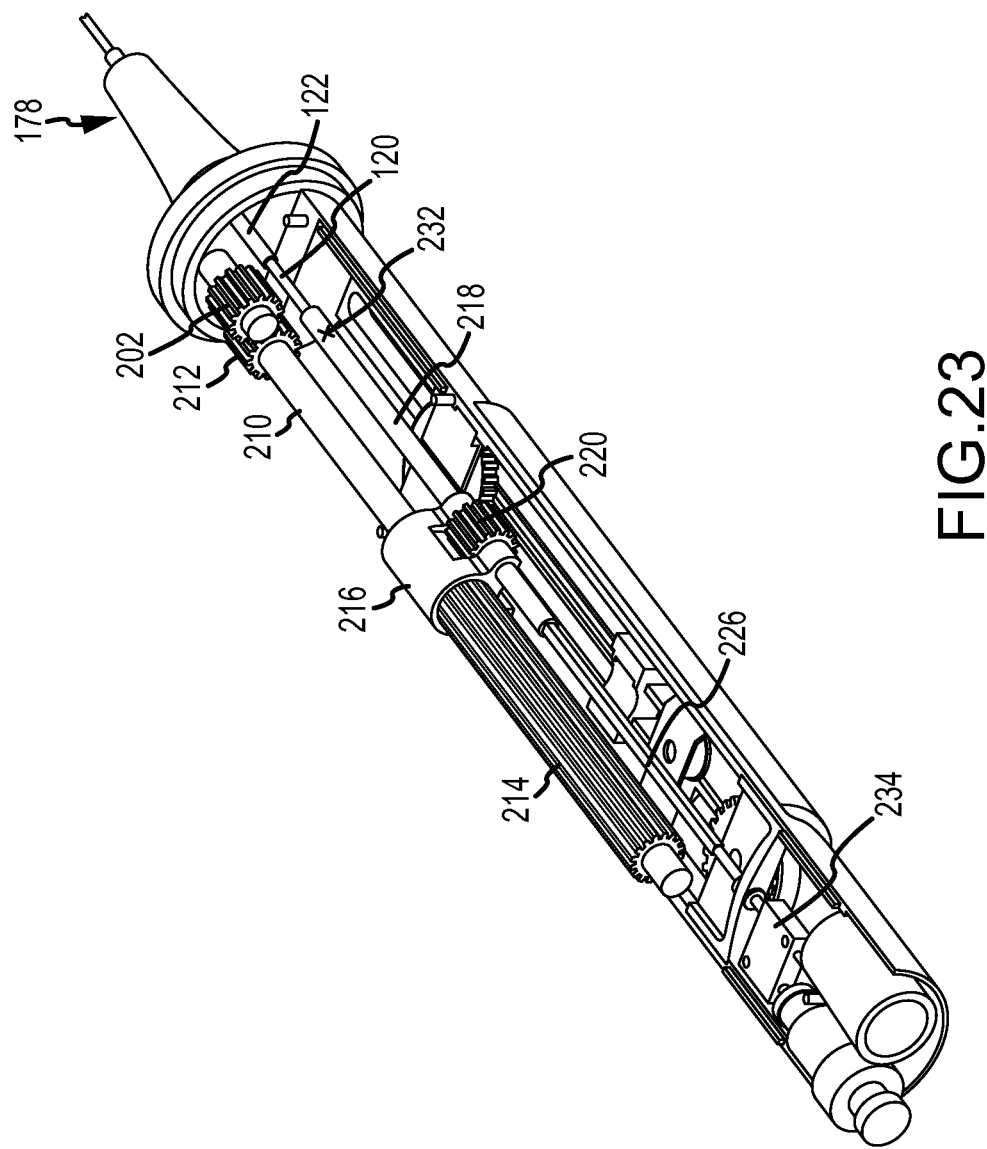
FIG. 23 is an isometric view of the handle of FIG. 21 taken from a different perspective and showing a first mechanism to impart rotational movement to the first (deformable) tubular component.

FIG. 23 is an isometric view of handle 112 from a perspective opposite that of FIG. 21. First mechanism 209 further includes a drive shaft 218 having a spur gear 220 in mesh with the spline gear portion 214 of spline shaft 210. Thus, rotation of spline shaft 210 causes rotation of drive shaft 218. Drive shaft 218 is configured for bi-directional rotation about its longitudinal axis. In addition, drive shaft 218 is configured for axial (linear) movement as well via movement of shuttle 216. As shown, even when there is linear movement of shuttle 216 along spline shaft 210, spur gear 220 remains in mesh with spline gear portion 214.

Figure 24:
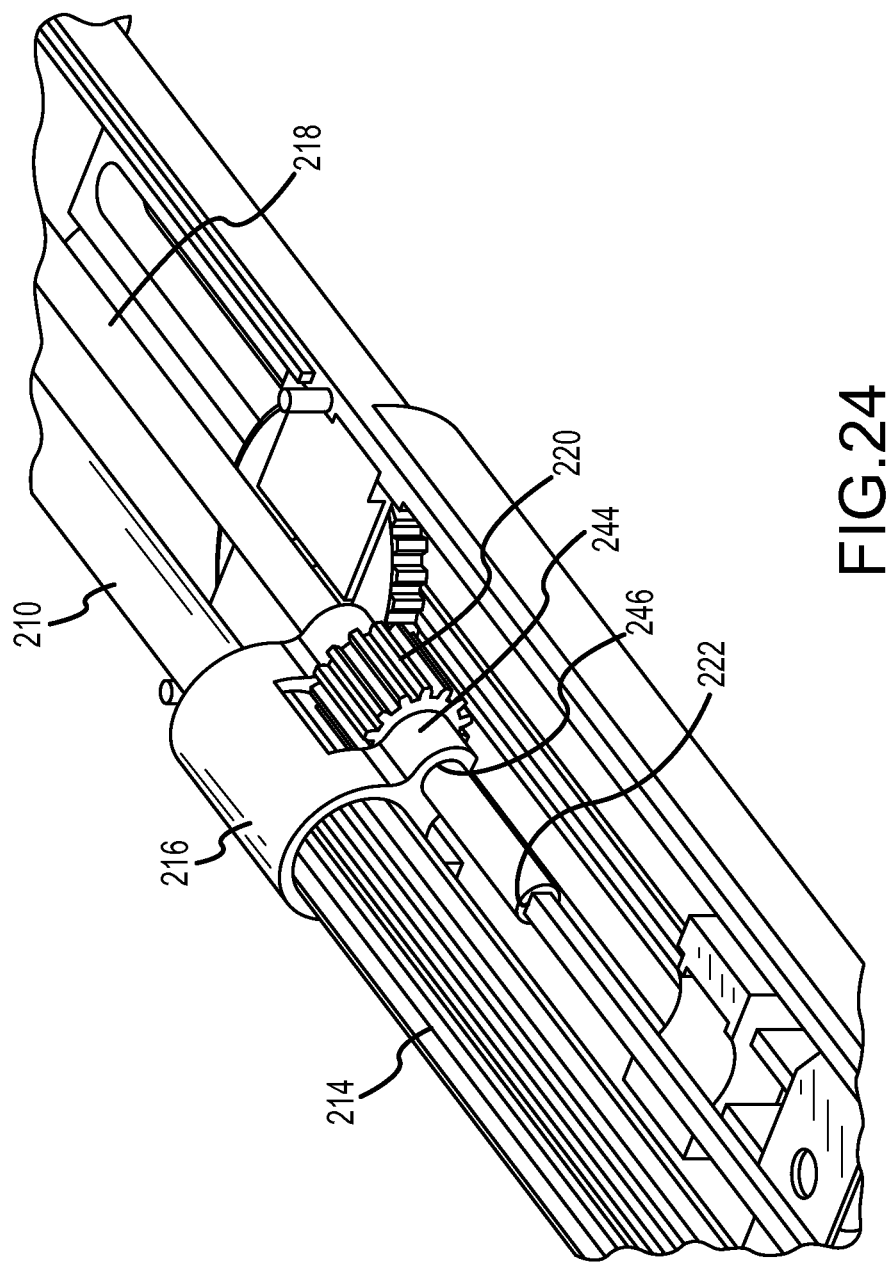
FIG. 24 is an enlarged view of FIG. 23.

FIG. 24 is an isometric view of handle 112 showing an enlarged portion of FIG. 23. Drive shaft 218 includes an internal keying arrangement, shown as an internal square socket 222 extending the axial length thereof.

Referring again to FIG. 23, shaft 122 is fixed to handle 112. Accordingly, shaft 122 will not rotate relative to handle 112, and will only rotate to the extent that handle 112 itself rotates. In addition, straight component 120 is attached to drive shaft 218 for rotation therewith.

Figure 25:
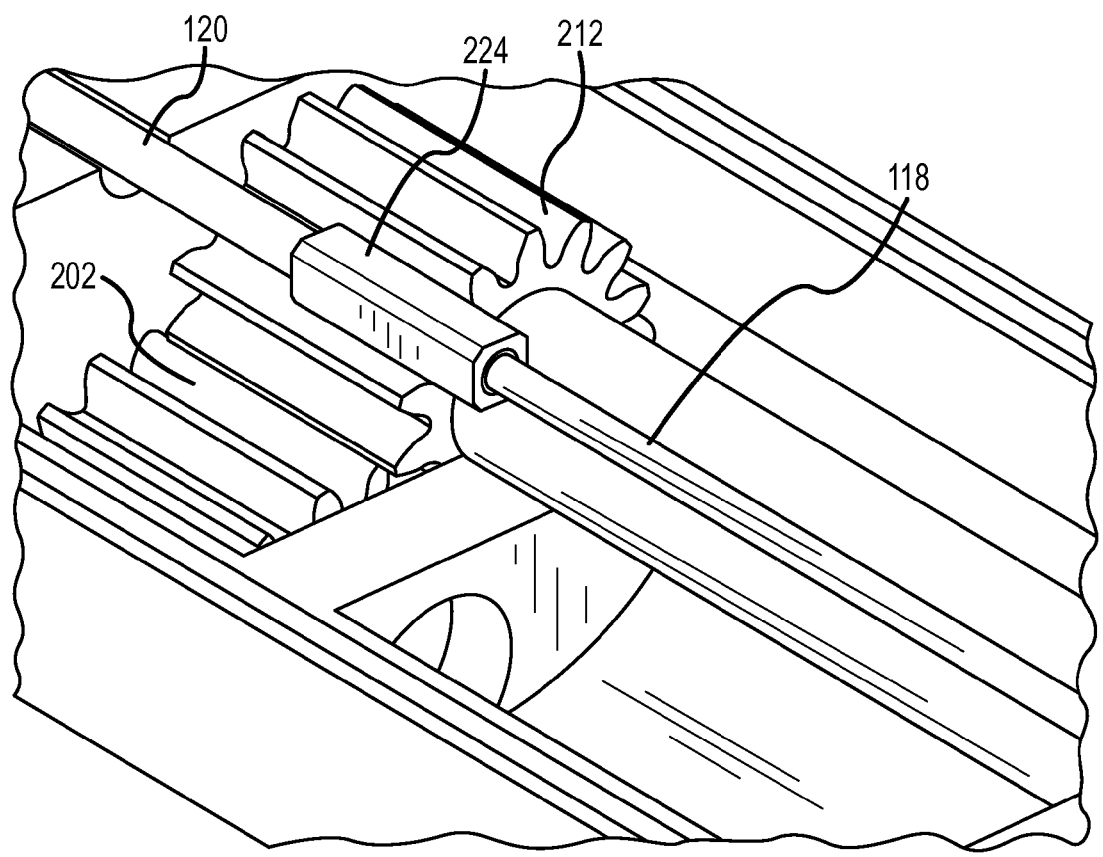
FIG. 25 is an isometric view of a first keying element used to join the second (straight) tubular component with the output of the first (rotational) mechanism of FIG. 23.

FIG. 25 is an enlarged bottom view of handle 112 showing straight component 120 being coupled to a first keying element 224. First component 118 axially extends beyond keying element 224. It should be appreciated that the attachment of first keying element 224 does not inhibit the relative sliding movement described above between components 118, 120. The keying element 224 is used to couple component 120 to drive shaft 218.

Figure 26:
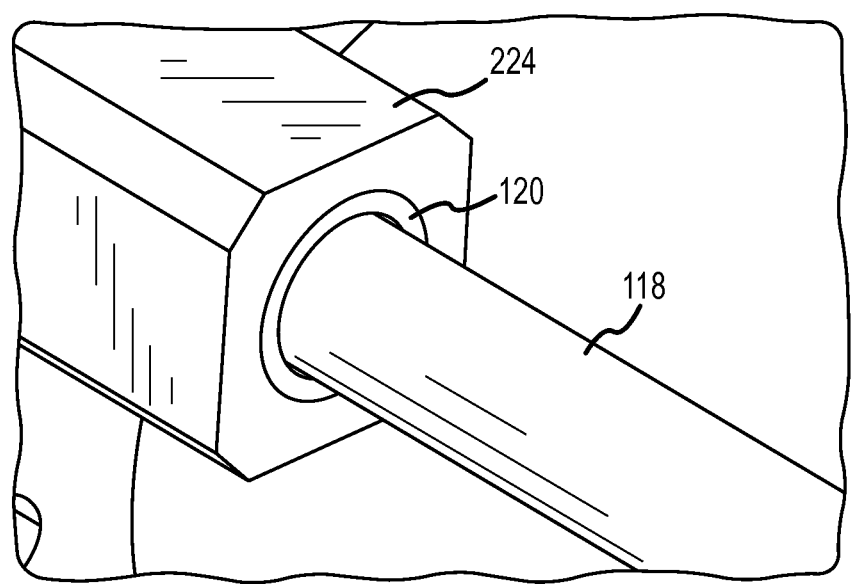
FIG. 26 is an enlarged view of the first keying element of FIG. 25.

FIG. 26 is an enlarged view of FIG. 25. As shown, the first keying element 224 has a substantially square profile is cross-section and is configured to correspond to and complement the internal keying arrangement 222 used by drive shaft 218 (shown in FIG. 24). Of course, variations are possible (e.g., hexagon, single flat, etc.).

Figure 27:
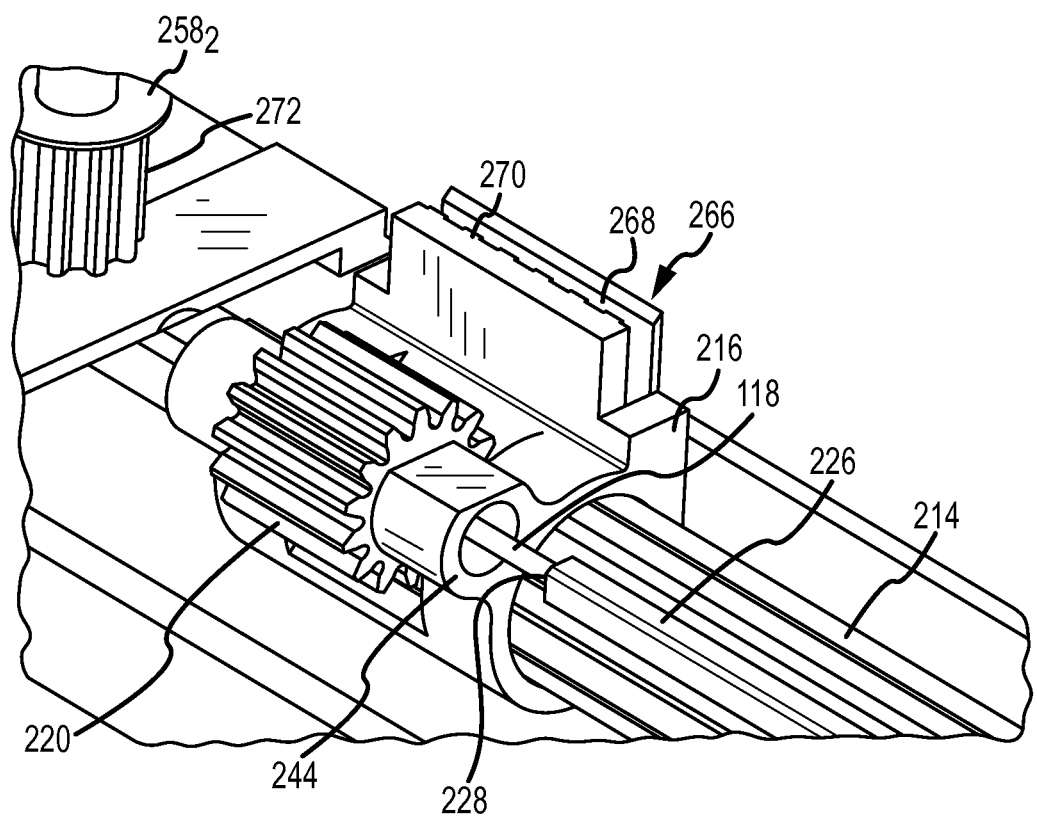
FIG. 27 is an isometric view of a second keying element and lumen extension.

FIG. 27 is an isometric view of a second keying element and lumen extension 226, which has a keyed outer profile configured to correspond to and complement internal keying arrangement 222. Extension 226 is connected (e.g., by welding) to the proximal end 228 of first component 118.

Figure 28:
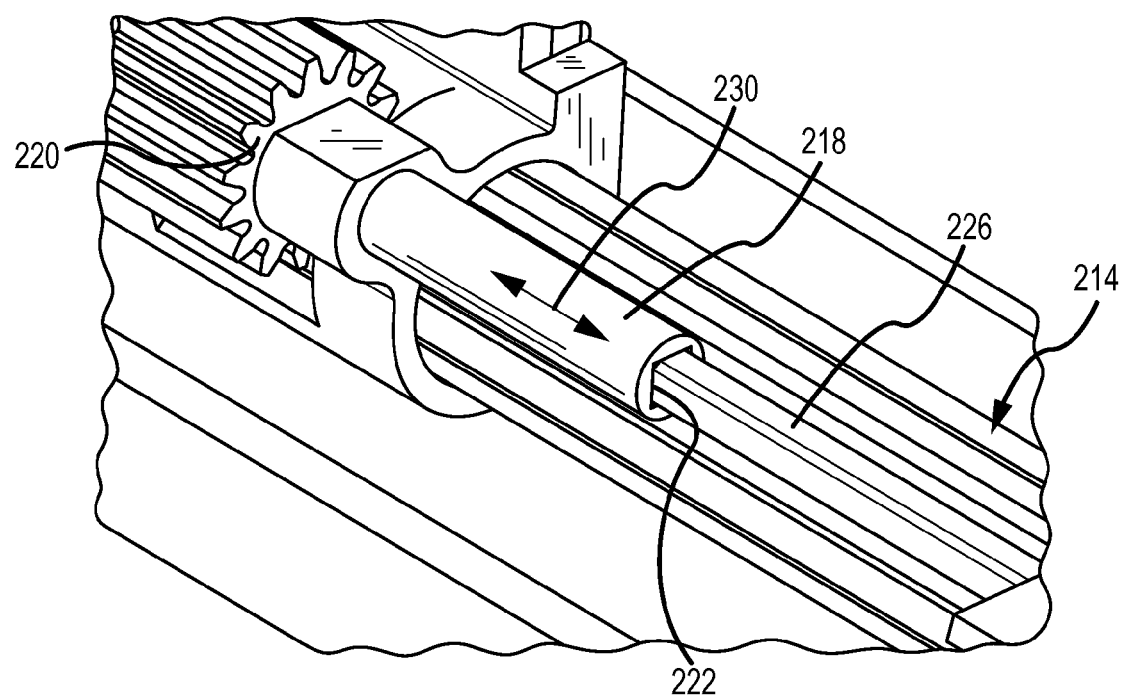
FIG. 28 is an enlarged isometric view of the second keying element of FIG. 27.

FIG. 28 is an isometric view, similar to FIG. 27, but including drive shaft 218 and showing square socket 222. As shown, second keying element and lumen extension 226 is received within drive shaft 218 but is not fixed thereto. Accordingly, while the keying arrangement is effective to enforce rotation of lumen extension 226 and component 118 together with drive shaft 218, drive shaft 218 can translate axially (direction 230) relative to lumen extension 226 and component 118. In other words, drive shaft 218 can move axially without also axially moving lumen 226 and component 118.

Referring again to FIG. 23, first keying element 224 (not shown), which itself is connected to straight tubular component 120, is connected to drive shaft 218 in a fixed relation. For example, first keying element 224 may be welded to drive shaft 218 at point 232. Accordingly, when drive shaft 218 rotates, so does first keying element 224, which in turn rotates straight tubular component 120 (and also component 118, as noted above). In addition, when drive shaft 218 is moved back and forth along its longitudinal axis, such axial movement also causes straight component 120 to axially move back and forth as well.

First component 118, which is connected to second keying element and lumen extension 226, is axially fixed relative to housing 176 by virtue of lumen extension 226 being axially anchored at manifold interface 234. However, due to the keyed arrangement, rotation of drive shaft 218 will also rotate lumen extension 226, also rotating component 118. Thus, when drive shaft 218 rotates, both components 118, 120 will rotate together with drive shaft 218. On the other hand, when drive shaft 218 is moved axially, component 120 will move axially but component 118 will not move axially, since the drive shaft 218 is configured to slide freely over and slide with respect to lumen extension 226.

Referring now to FIGS. 21-28, in operation of first mechanism 209, when the user rotates knob 184, a corresponding rotation will be imparted to input gear 202. Input gear 202 is in mesh with transfer gear 212, which in turn causes spline shaft 210 to rotate, including spline gear portion 214. Spline gear portion 214 is in mesh with spur gear 220, and thus rotation of spline shaft 210 also rotates spur gear 220 as well. Rotation of spur gear 220 causes drive shaft 218 to rotate. Rotation of drive shaft 218 causes both first and second components 118, 120 to rotate. When a user reverses the rotational direction of knob 184 (i.e., either clockwise or counter-clockwise), a corresponding change in rotational direction occurs with respect to components 118, 120. Through the foregoing, relative rotation of component 118 (and component 120) may be accomplished manually using handle 112, thereby allowing user-determined adjustments in the orientation of section 128, for example, as described and illustrated above in connection with FIGS. 15A-15F. Accordingly, first mechanism 209 is responsive to a rotational input to effect a relative rotation of component 118 (and component 120).

Figure 29:
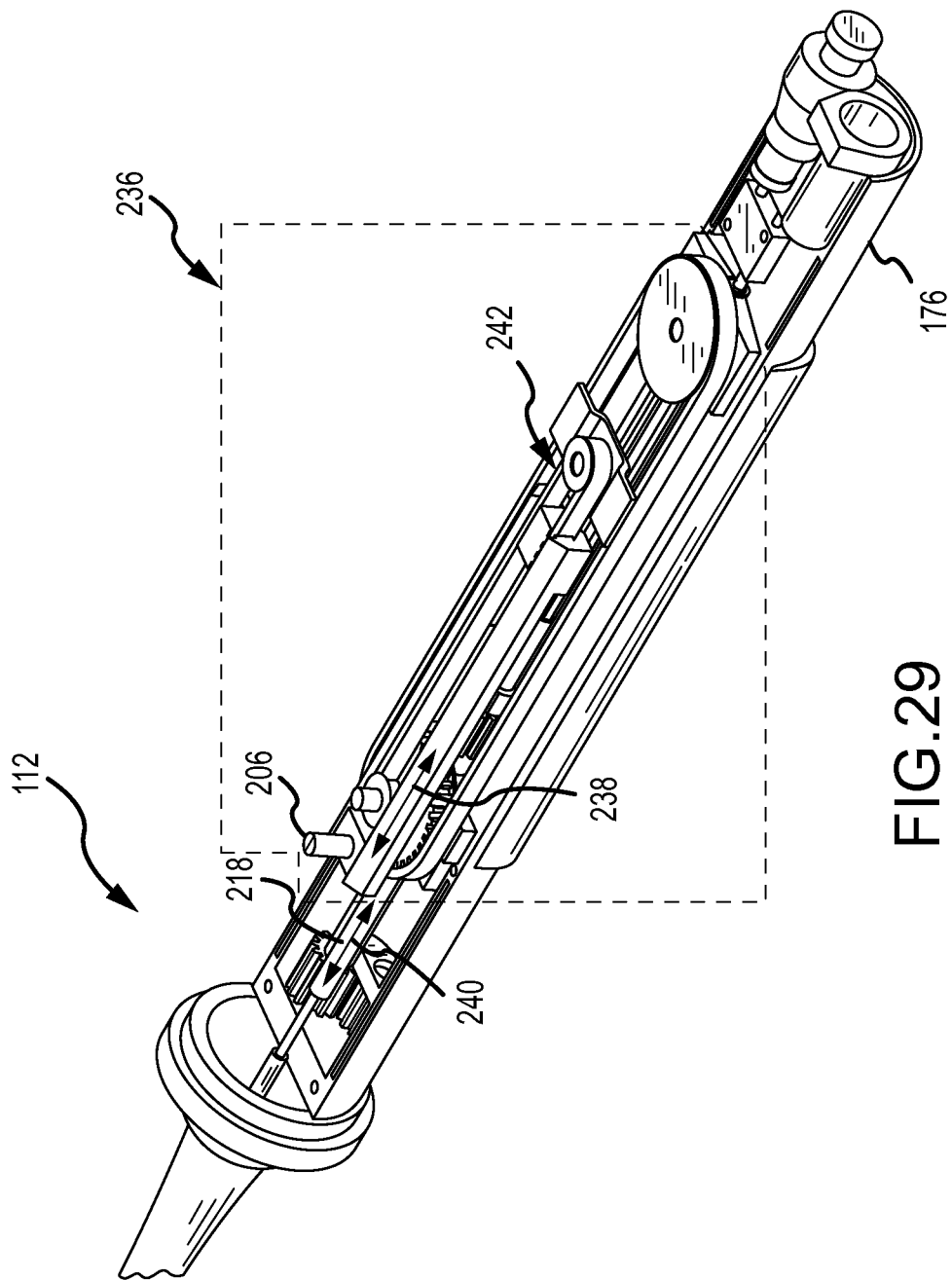
FIG. 29 is a bottom isometric view of the handle of FIG. 17, with a bottom portion of the housing omitted, showing a second mechanism for imparting a relative linear movement to the second (substantially "straight") tubular component.

FIG. 29 is an isometric bottom view of handle 112, which includes a second mechanism 236 configured to effect a linear displacement of straight component 120 relative to first component 118. In general, second mechanism 236 is responsive to a linear movement of input pin 206, which input movement is shown as input movement 238 in FIG. 29. Second mechanism 236 is responsive to movement 238 for producing a linear movement of drive shaft 218. The corresponding linear movement is designated as output movement 240 in FIG. 29. In an embodiment, second mechanism 236 is configured with an input/output transfer ratio such that a unit of input movement produces multiple units of output movement (e.g., 1:3 such that a ¼" input movement results in an output movement of ¾", etc.). Thus the transfer ratio may be about one or greater than about one. In alternate embodiments, the transfer ratio may be less than one. Second mechanism 236 also shares shuttle 216 with first mechanism 209 and further includes a transmission 242. As already described above in connection with FIG. 21, shuttle 216 is configured to move spur gear 220 along spline gear portion 214. The transmission 242 is coupled between input pin 206 and shuttle 216 and is responsive to first linear movement 238 to cause second linear movement 240 of shuttle 216. Thus, movement of shuttle 216 causes drive shaft 218 to be translated by second linear movement 240, which in turn axially moves first component 118 by the same linear movement 240.

Referring again to FIG. 24, shuttle 216 includes a U-shaped collar 244 that surrounds spur gear 220. The collar 244 constrains free movement of spur gear 220 and drive shaft 218 in an axial direction such that movement of shuttle 216 along spline gear portion 214 moves spur gear 220 and drive shaft 218 in a likewise axial (linear) direction. However, collar 244 is also configured to allow free rotation of the spur gear 220 and drive shaft 218 due to a clearance 246 between the outside diameter of drive shaft 218 and the inside diameter of a through-hole in collar 244. The following Figures will illustrate how the transmission 242 moves shuttle 216.

Figure 30:
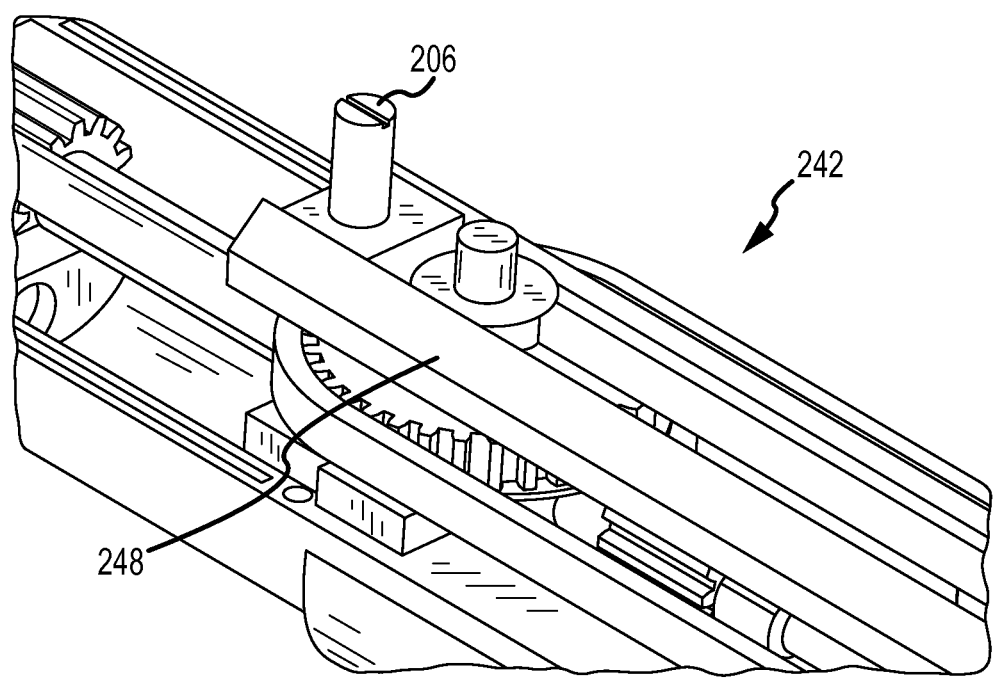
FIG. 30 is an enlarged isometric view of the second mechanism of FIG. 29, showing the input pin.
Figure 31:
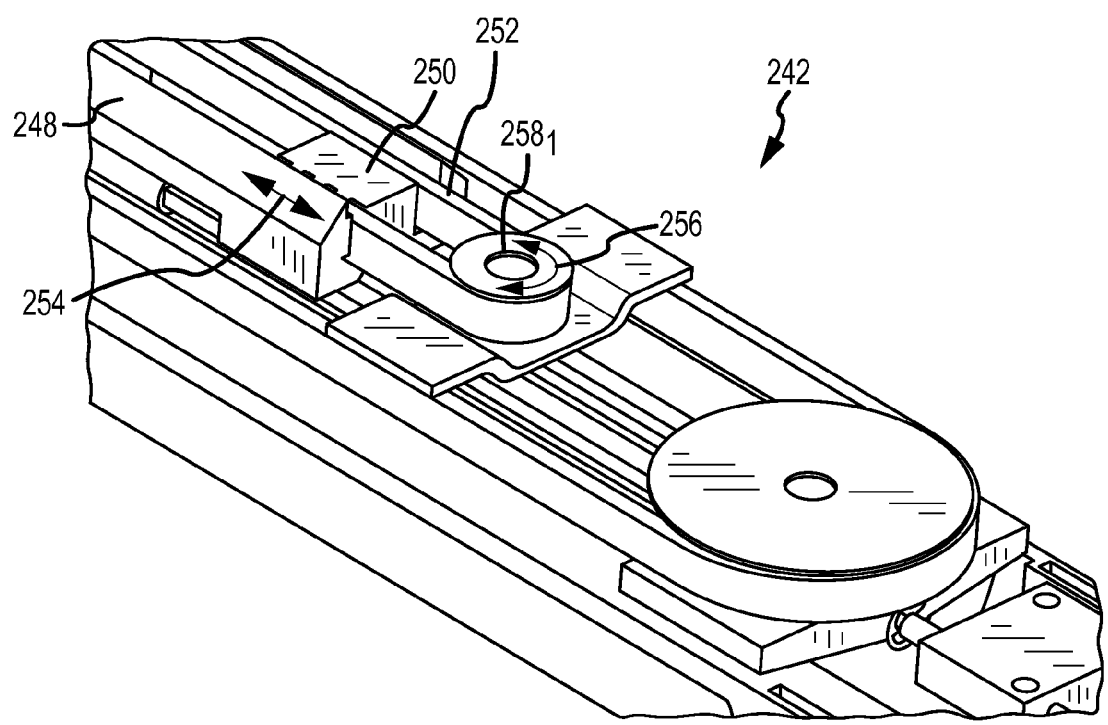
FIG. 31 is an enlarged isometric view of the second mechanism of FIG. 29, showing a transmission.

FIGS. 30-31 are isometric, enlarged views of transmission 242. Transmission 242 includes a carriage 248 configured to move linearly with the linear movement of input pin 206. Carriage 248 is substantially rigid and extends generally along the main axis of housing 176. Carriage 248 includes a first end from which projects input pin 206 and a second, opposing end terminating in a first belt clamp 250. Transmission 242 further includes a primary belt 252. First belt clamp 250 may include teeth or other known features configured to fix belt 252 with carriage 248 for movement together. Transmission 242 further includes a first pair or set of pulleys $258_1$ and $258_2$ (best shown in FIG. 32). The linear movement 254 of carriage 248 results in a corresponding rotary movement 256 of pulleys $258_1$ and $258_2$ (by virtue of belt 252 coupling the pair of pulleys together).

Figure 32:
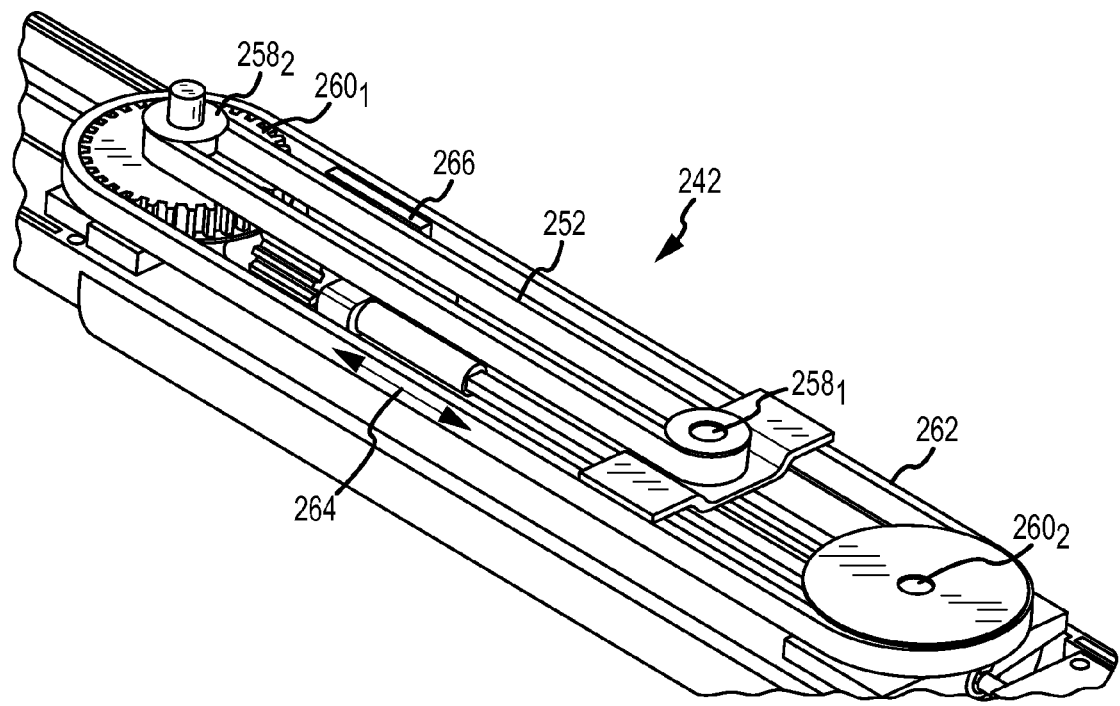
FIG. 32 is a bottom isometric view of the second mechanism of FIG. 29, with portions omitted.

FIG. 32 is a further isometric view of transmission 242. Transmission 242 further includes a second set of pulleys $260_1$ and $260_2$ wherein one of the pulleys (i.e., pulley $260_1$) is configured to rotate with a pulley from the first set of pulleys $258_1$ and $258_2$ (in this case pulley $258_2$). In other words, as shown, pulley $260_1$ rotates together with pulley $258_2$. Transmission 242 further includes a secondary belt 262 on the second set of pulleys $260_1$ and $260_2$. Pulleys $260_1$ and $260_2$ rotate together by virtue of secondary belt 262. Note that a first diameter of the first set of pulleys $258_1$ and $258_2$ is smaller by a predetermined factor than a second diameter of the second set of pulleys $260_1$ and $260_2$. In the illustrated embodiment, a pulley ratio of the second diameter to the first diameter is larger than one, and in one embodiment, the ratio may be about three (3). This mechanical advantage results in an amplification of the linear movement of knob 184 and the resulting linear movement 264 of secondary belt 262, and thus ultimately of the linear movement of straight component 120. Shuttle 216 (partially hidden in FIG. 32) is coupled by way of a secondary belt clamp 266 to move with the movement 264 of secondary belt 262.

Referring again to FIG. 27, secondary belt clamp 266 is generally U-shaped having a central void 268 configured in size and shape to receive secondary belt 262 (belt 262 omitted for clarity in FIG. 27). Clamp 268 may include teeth 270 or the like to facilitate a secure coupling between secondary belt 262 and clamp 268 (and thus also with shuttle 216). As also shown in FIG. 27, pulley $258_2$ may be configured to rotate with pulley $260_1$ (best shown in FIG. 32) by incorporating an external gear 272 that is locked with a corresponding internal circumference gear (not show) provided on an inner circumference of pulley $260_1$.

Figure 33:
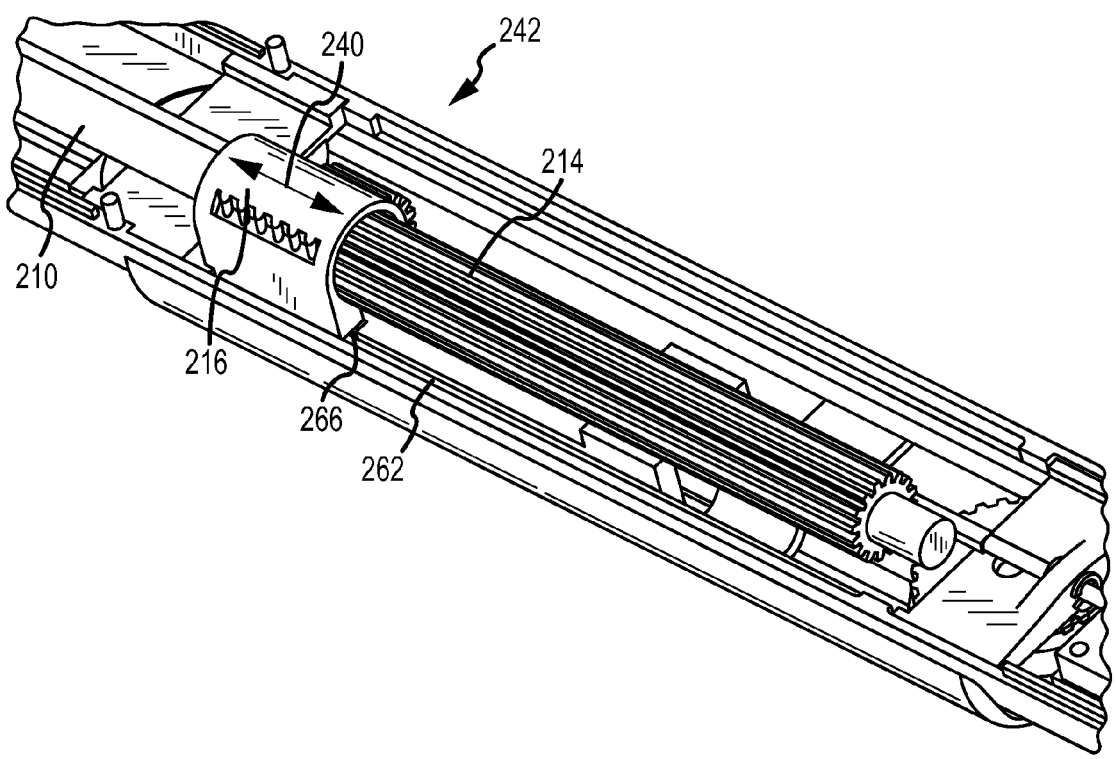
FIG. 33 is a top, isometric view of the second mechanism of FIG. 29.

FIG. 33 is a top, isometric view of transmission 242, showing the connection of secondary belt 262 to shuttle 216 by way of secondary belt clamp 266. The movements of belt 262 linearly move shuttle 216 in the directions designated by double arrow-headed line 240.

Referring to FIGS. 24, 27 and 29-33, and in operation of second mechanism 236, when a user linearly (axially) moves knob 184, a corresponding linear movement will be imparted to input pin 206. Input pin 206 is firmly coupled to transmission 242. More specifically, pin 206 is fixed to carriage 248, so that a linear movement of input pin 206 causes a corresponding linear movement of carriage 248. Linear movement of carriage 248 causes a corresponding movement of primary belt 252 coupled on and around pulleys $258_1$ and $258_2$, which rotate with the movement of primary belt 252. Rotation of pulley $258_2$ rotates pulley $260_1$, which are locked together and both rotate on the same axis. A secondary belt 262 disposed on and around pulleys $260_1$, $260_2$ moves with the rotation of pulleys $260_1$, $260_2$. The shuttle 216 is coupled to move with the movement of secondary belt 262. The movement of shuttle 216 linearly moves spur gear 220, and thus also linearly moves drive shaft 218. Since straight component 120 is rigidly coupled to drive shaft 218, component 120 also moves axially. Through the foregoing, relative axial movement of component 120 may be accomplished manually (axially) by moving knob 184, thereby allowing user-determined adjustments in the deflection angle of curvilinear section 128. Accordingly, second mechanism 236 is responsive to a linear input to effect a relative linear displacement of component 120.

When a user rotates and linearly moves knob 184, both first and second mechanisms 209, 236 are actuated to adjust both the deflection angle as well as the orientation of the catheter distal tip, thereby achieving omni-directional deflection without pull wires, without rotation of the outer shaft and without compression of the shaft (due to repeated deflections using pull wires).

Figure 34:
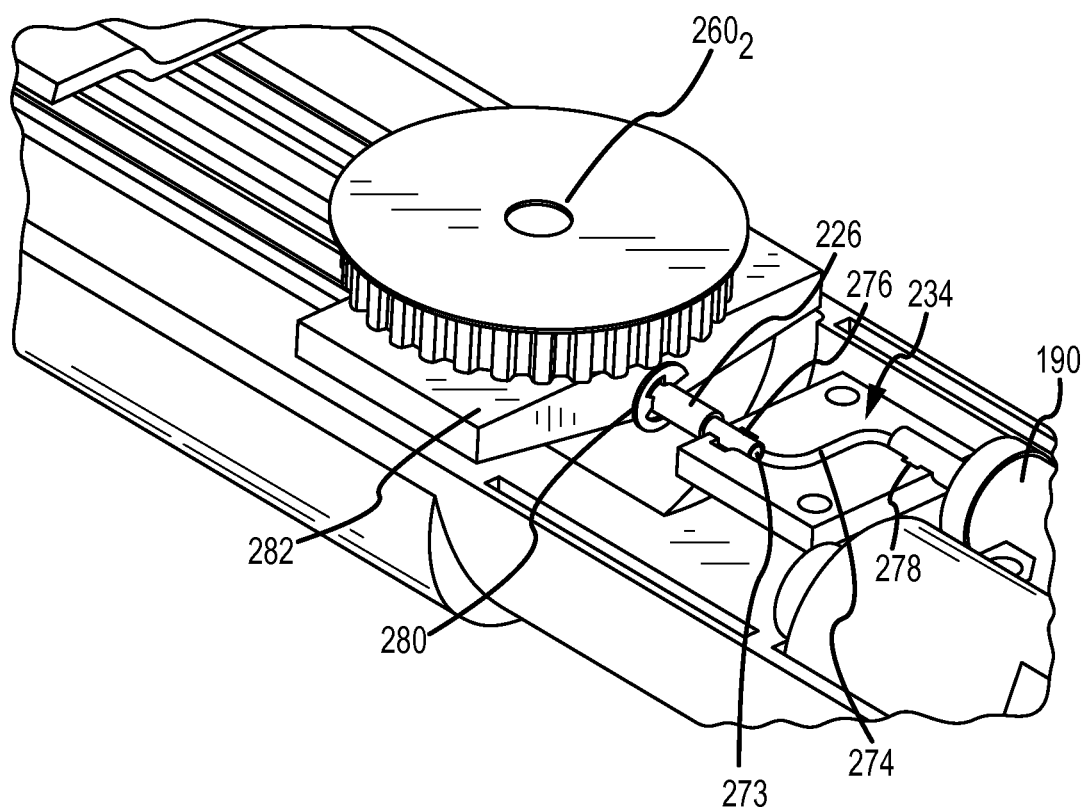
FIG. 34 is a bottom, isometric view of the proximal end of the housing, showing an irrigation fluid manifold interface.

FIG. 34 is a bottom isometric view of handle 112 showing manifold interface 234 in greater detail. As described above, lumen extension 226 is coupled to component 118, which includes central lumen 134 (FIG. 6) for carrying irrigation fluid from the proximal end portion 106 of shaft assembly 102 to distal end portion 108. Lumen extension 226 includes a lumen 273 for establishing fluid communication between manifold interface 234 and central lumen 134. Interface 234 in the illustrated embodiment comprises a top piece (shown in FIG. 23) and a mating bottom piece (shown in FIG. 34, with the top piece omitted). The top and bottom pieces include internal channel work which cooperate form a channel 274 for the transport of irrigation fluid. The manifold interface 234 further includes an outlet configured to receive a proximal end portion of lumen extension 226, which may include a fluid seal, such as an O-ring seal 276 or the like. Manifold interface 234 also includes an inlet configured to receive inlet irrigation port 190, which may include a fluid seal, such as an O-ring seal 278 or the like. FIG. 34 also shows a C-clip 280 configured to position lumen extension 226 relative to a support 282. C-clip 280 allows lumen extension 226 to rotate but otherwise facilitates axial anchoring of lumen extension 226.

Embodiments of catheters including those with catheter shafts as generally illustrated and discussed above exhibit excellent column strength and torsional strength, which allow configurations that do not include a compression coil or any planarity members. While the embodiments illustrated and described above do not include a mechanical tensioning deflection elements (e.g., pull wires), certain embodiments may include one or more such elements, for example, to achieve complex shapes. In addition, certain embodiments may optionally include a safety wire or the like which is attached to a distal end electrode or other distal structures and extends to the proximal end of the catheter to secure such distal structure (e.g., to assist withdrawal). In an exemplary embodiment, a high tensile strength LCP (liquid crystal polymer) fiber wire may be used as the safety wire or alternatively may comprise a high strength fibrous material, for example, a para-aramid synthetic fiber commercially available under the trademark KEVLAR® from E.I. du Pont de Nemours and Company, Wilmington, Del., U.S.A.

Embodiments of catheters, including those with catheter shafts as generally illustrated and discussed above, may be readily incorporated with or integrated into catheter 100 for performing ablative procedures. Other types of energy sources (i.e., other than radio-frequency—RF energy) may also be used in connection with catheter 100, such as ultrasound (e.g. high-intensity focused ultrasound (HIFU)), laser, cryogenic, chemical, photo-chemical or other energy used (or combinations and/or hybrids thereof) for performing ablative procedures. Additional electrode tips may be used and configured, such as a closed loop cooled tip. Further configurations, such as balloon-based delivery configurations, may be incorporated into catheter 100 in any particular embodiment. Furthermore, various sensing structures may also be included in catheter 100, such as temperature sensor(s), force sensors, various localization sensors (see description above), imaging sensors and the like.

Although a number of embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter configured for omni-directional deflection of a distal portion, comprising:
    a first tubular component having a distal portion and a proximal portion, said proximal portion being substantially linear in shape and said distal portion including a preformed curvilinear section;
    a second tubular component having a distal portion and a proximal portion, said second component being configured for individual slidable movement and common rotational movement relative to said first component, to thereby allow said distal portion of said second component to slidably bear against said preformed curvilinear section of said first component;

a shaft having a shaft orientation and a distal portion and a proximal portion and an inner lumen configured to accommodate said first and second tubular components;

a controller at a proximal end of said shaft and including a base and configured (i) to effect a relative axial movement between said first and second tubular components and (ii) to effect a rotational movement of said first component and said second component relative to said shaft while said shaft orientation remains in a fixed rotational position relative to said base, said base comprising a handle housing, said controller including a knob configured for manual actuation wherein said knob comprises a ring disposed radially outwardly of said handle housing, wherein said knob is configured for movement relative to said handle housing, said controller being responsive to actuation of said knob to effect said relative axial movement and said rotational movement, wherein said first and second components are in a relation selected from the group comprising a first concentric arrangement where said first tubular component is received within a central lumen of said second tubular component; and a second concentric arrangement where said second component is received within a central lumen of said first tubular component, said first and second components are concentric with said shaft over said proximal portion of said shaft including said proximal end and said distal portion of said shaft.

2. The catheter of claim 1 wherein said preformed curvilinear section comprises a regular shape comprising one of a C-shape, an S-shape, a circular shape and a multi-revolution shape.

3. The catheter of claim 1 wherein when said movement of said second component is in a first direction towards a distal end of said first component, said distal portion of said second component progressively deflects said preformed curvilinear section towards an axis of said first component.

4. The catheter of claim 3 wherein an amount said curvilinear section deflects corresponds to an axial position of said second component relative to said preformed curvilinear distal section.

5. The catheter of claim 3 wherein when said movement of said second component is in a second direction opposite said first direction and away from said distal end of said first component, said second component distal portion progressively disengages said preformed curvilinear section allowing said curvilinear section to progressively deflect away from said axis to assume a preformed shape.

6. The catheter of claim 1 wherein said distal portion of said second component is more rigid than said preformed curvilinear distal section.

7. The catheter of claim 1 wherein said shaft comprises braided thermoplastic.

8. The catheter of claim 1 wherein said preformed curvilinear distal section comprises a shape memory material.

9. The catheter of claim 8 wherein said shape memory material comprises Nitinol material.

10. The catheter of claim 1 wherein said shaft includes a relatively flexible distal segment and comprising at least one of an electrode, a sensor and a transducer configured to perform a respective one of at least a diagnostic and therapeutic function.

11. The catheter of claim 1 wherein said controller is housed in a robotically-actuated catheter system.

12. A catheter configured for omni-directional deflection of a distal portion, comprising:

a first tubular component having a distal portion and a proximal portion, said proximal portion being substantially linear in shape and said distal portion including a preformed curvilinear section;

a second tubular component having a distal portion and a proximal portion, said second component being configured for individual slidably movement and common rotational movement relative to said first component, to thereby allow said distal portion of said second component to slidably bear against said preformed curvilinear section of said first component;

a shaft having a shaft orientation and a distal portion and a proximal portion and an inner lumen configured to accommodate said first and second tubular components;

a controller at a proximal end of said shaft and including a base and configured (i) to effect a relative axial movement between said first and second tubular components and (ii) to effect a rotational movement of said first component and said second component relative to said shaft while said shaft orientation remains in a fixed rotational position relative to said base, wherein said first and second components are in a relation selected from the group comprising a first concentric arrangement where said first tubular component is received within a central lumen of said second tubular component; and a second concentric arrangement where said second component is received within a central lumen of said first tubular component, said first and second components are concentric with said shaft over said proximal portion of said shaft including said proximal end and said distal portion of said shaft; and wherein said controller is housed in a catheter handle disposed at a catheter proximal end, said base comprising a handle housing, and wherein said shaft is fixed relative to said housing, said controller including a knob configured for manual actuation, said controller further including a first mechanism responsive to actuation of said knob configured to axially move said second tubular component relative to said first tubular component, and wherein said housing has an axis associated therewith, said first tubular component is axially fixed relative to said housing so that said first tubular component will not move axially relative to said housing.

13. A catheter configured for omni-directional deflection of a distal portion, comprising:

a first tubular component having a distal portion and a proximal portion, said proximal portion being substantially linear in shape and said distal portion including a preformed curvilinear section;

a second tubular component having a distal portion and a proximal portion, said second component being configured for individual slidable movement and common rotational movement relative to said first component, to thereby allow said distal portion of said second component to slidably bear against said preformed curvilinear section of said first component;

a shaft having a shaft orientation and a distal portion and a proximal portion and an inner lumen configured to accommodate said first and second tubular components;

a controller at a proximal end of said shaft and including a base and configured (i) to effect a relative axial movement between said first and second tubular components and (ii) to effect a rotational movement of said first component and said second component while said shaft orientation remains in a fixed rotational position relative to said base, wherein said first and second components are in a relation selected from the group comprising a first concentric arrangement where said first tubular component is received within a central lumen of said second tubular component; and a second concentric arrangement where said second component is received within a central lumen of said first tubular component, said first and second components are concentric with said shaft over said proximal portion of said shaft including said proximal end and said distal portion of said shaft, said controller is housed in a catheter handle disposed at a catheter proximal end, said base comprising a handle housing, said shaft is fixed relative to said housing, said controller including a knob configured for manual actuation, said controller further including a first mechanism responsive to actuation of said knob configured to axially move said second tubular component relative to said first tubular component, and wherein said controller further includes a second mechanism responsive to actuation of said knob configured to rotate said first tubular component relative to said housing.

14. A catheter configured for omni-directional deflection of a distal portion, comprising:

a first tubular component having a distal portion and a proximal portion, said proximal portion being substantially linear in shape and said distal portion including a preformed curvilinear section;

a second tubular component having a distal portion and a proximal portion, said second component being configured for individual slidable movement and common rotational movement relative to said first component, to thereby allow said distal portion of said second component to slidably bear against said preformed curvilinear section of said first component;

a shaft having a shaft orientation and a distal portion and a proximal portion and an inner lumen configured to accommodate said first and second tubular components;

a controller at a proximal end of said shaft and including a base and configured (i) to effect a relative axial movement between said first and second tubular components and (ii) to effect a rotational movement of said first component and said second component while said shaft orientation remains in a fixed rotational position relative to said base, wherein said first and second components are in a relation selected from the group comprising a first concentric arrangement where said first tubular component is received within a central lumen of said second tubular component; and a second concentric arrangement where said second component is received within a central lumen of said first tubular component, said first and second components are concentric with said shaft over said proximal portion of said shaft including said proximal end and said distal portion of said shaft, said controller is housed in a catheter handle disposed at a catheter proximal end, said base comprising a handle housing, said shaft is fixed relative to said housing, said controller including a knob configured for manual actuation, said controller further including a first mechanism responsive to actuation of said knob configured to axially move said second tubular component relative to said first tubular component, and wherein said housing has a cylindrical portion, said knob comprising an elongate ring radially outwardly of said cylindrical portion and wherein said ring has an internal gear disposed in an inner circumference thereof, a second mechanism including an input gear in mesh with said internal gear of said knob such that rotation of said knob causes rotation of said input gear.

15. A method of making a catheter configured for omni-directional deflection of a distal portion, comprising the steps of:

producing a first tubular component having a distal portion and a proximal portion, said proximal portion being substantially linear in shape and the distal portion including a preformed curvilinear section;

producing a second tubular component having a distal portion and a proximal portion;

coupling the first and second components so as to allow individual slidable movement and common rotational movement, to thereby allow the distal portion of the second component to slidably bear against the preformed curvilinear section of the first component, wherein coupling comprises disposing the first and second components in a relation selected from the group comprising (i) a first concentric arrangement where said first tubular component is received within a central lumen of said second tubular component; and (ii) a second concentric arrangement where said second component is received within a central lumen of said first tubular component;

disposing the first and second components in an inner lumen of a shaft to thereby produce a shaft assembly such that the first and second components and the shaft are concentric over a proximal portion of the shaft including a proximal end thereof and a distal portion of the shaft; and coupling the shaft assembly to a controller such that the shaft is in a predetermined shaft orientation relative to the controller and wherein the controller is configured (i) to effect a relative axial movement between the first and second tubular components and (ii) to effect a rotational movement of the first and second components relative to said shaft while the shaft orientation remains fixed relative to said controller, said controller being disposed at the proximal end of said shaft, said controller comprising a handle housing and a knob configured for manual actuation wherein said knob comprises a ring disposed radially outwardly of said handle housing, wherein said knob is configured for movement relative to said handle housing, said controller responsive to actuation of said knob to effect said relative axial movement and said rotational movement.

16. A method of operating a catheter for omni-directional deflection of a distal portion, comprising the steps of:

disposing a first component of the catheter and a second component of the catheter in a relation selected from the group comprising (i) a first concentric arrangement where the first component is received within a central lumen of the second component; and (ii) a second concentric arrangement where the second component is received within a central lumen of the first component;

imparting, with respect to a preformed curvilinear section at a distal end of the first component, a relative slidable axial movement to the second component that is substantially straight so as to vary where a distal end portion of the second component bears against the preformed curvilinear section, thereby altering a shape of the preformed curvilinear section, and wherein the first and second components are concentric with a shaft over a proximal portion including a proximal end of the shaft and a distal portion of the shaft; and rotating the first and second components relative to said shaft while maintaining a shaft orientation of the shaft of the catheter in which the first and second components are disposed in a fixed position relative to a controller located at the proximal end of the shaft operative to effect said rotating wherein said rotating alters an orientation of the preformed curvilinear section, wherein said controller comprises a handle housing and a knob configured for manual actuation wherein the knob comprises a ring disposed radially outwardly of the handle housing, wherein said knob is configured for movement relative to said handle housing, and wherein said imparting a relative slidable axial movement and said rotating the first and second components are responsive to actuation of the knob.

17. The method of claim 16 wherein said imparting step includes the sub-step of:

moving the second component in a first axial direction towards the distal end of the first component wherein the second component progressively deflects the preformed curvilinear section towards an axis of the first component.

18. The method of claim 17 wherein said moving sub-step includes deflecting the preformed curvilinear section by an amount that corresponds to an axial position of the second component relative to the preformed curvilinear section.

19. The method of claim 17 wherein said imparting step includes the sub-step of:

moving the second component in a second axial direction opposite the first axial direction and away from the distal end of the first component wherein the second component progressively disengages the preformed curvilinear section thereby allowing the curvilinear section to progressively deflect away from the axis.

20. The method of claim 16 wherein the shaft is fixed relative to a housing of the controller.

21. A catheter configured for omni-directional deflection of a distal portion, comprising:

a shaft assembly including a first component having a preformed curvilinear section, a substantially straight second component slidably disposed with respect to said first component, and a shaft with an inner lumen configured to accommodate said first and second components wherein said first and second components are in a relation selected from the group comprising a first concentric arrangement where said first tubular component is received within a central lumen of said second tubular component; and a second concentric arrangement where said second component is received within a central lumen of said first tubular component, and wherein said first and second components are concentric with said shaft over a proximal portion including a proximal end of said shaft and a distal portion of said shaft;

means disposed at said proximal end of said shaft for imparting a relative axial movement of said second component with respect to said preformed curvilinear section so as to vary a position where a distal end portion of said second component bears against said preformed curvilinear section, thereby altering a shape of said preformed curvilinear section; and means disposed at said proximal end of said shaft for rotating said first and second components relative to said shaft while maintaining a shaft orientation of said shaft in a fixed position relative to said rotating means, thereby altering an orientation of said preformed curvilinear section, wherein said means for imparting a relative axial movement and said means for rotating said first and second components comprise a handle housing and a knob configured for manual actuation wherein said knob comprises a ring disposed radially outwardly of said handle housing, wherein said knob is configured for movement relative to said handle housing, said means for imparting a relative axial movement and said means for rotating said first and second components being responsive to actuation of said knob to effect said relative axial movement and said rotating of said first and second components.

22. The catheter of claim 21 wherein said imparting means includes means for moving said second component in a first axial direction towards a distal end of said first component wherein said distal end portion of said second component progressively deflects said preformed curvilinear section towards an axis of said first component.

23. The catheter of claim 22 wherein said moving means is further configured for moving said second component in a second axial direction opposite said first axial direction and away from said distal end of said first component wherein said second component progressively disengages said preformed curvilinear section thereby allowing said curvilinear section to progressively deflect away from said axis.

* * * * *